US012622645B2

(12) United States Patent     (10) Patent No.:   US 12,622,645 B2

Reiner     (45) Date of Patent:     May 12, 2026

(54) SIGNAL-EMITTING AND RECEIVING MEDICAL DEVICES WHICH PROVIDE DATA FOR REAL-TIME MULTI-DIMENSIONAL ANATOMIC VISUALIZATION MAPS

(71) Applicant: Bruce Reiner, Berlin, MD (US)

(72) Inventor: Bruce Reiner, Berlin, MD (US)

( * ) Notice: Subject to any disclaimer, the term of this patent is extended or adjusted under 35 U.S.C. 154(b) by 880 days.

(21) Appl. No.: 17/836,742

(22) Filed: Jun. 9, 2022

(65) Prior Publication Data

US 2022/0304626 A1     Sep. 29, 2022

Related U.S. Application Data

(63) Continuation-in-part of application No. 17/712,693, filed on Apr. 4, 2022, now Pat. No. 11,974,861, and (Continued)

(51) Int. Cl.
    *A61B 5/00*     (2006.01)
    *A61B 1/00*     (2006.01)
    (Continued)

(52) U.S. Cl.
    CPC ........ *A61B 5/6861* (2013.01); *A61B 1/00016* (2013.01); *A61B 1/00097* (2022.02); *A61B 5/07* (2013.01); *A61B 34/30* (2016.02); *A61B 1/041* (2013.01); *A61B 10/04* (2013.01); *A61B 2017/00221* (2013.01);
    (Continued)

(58) Field of Classification Search
    CPC ....... A61B 5/07; A61B 5/6861; A61B 5/0205; A61B 5/145; A61B 5/1455; A61B 5/067;

A61B 5/14503; A61B 5/6867; A61B 2562/0285; A61B 2034/2051; A61B 2034/2055; A61B 2034/2063
See application file for complete search history.

(56) References Cited

U.S. PATENT DOCUMENTS 5,596,988 A    1/1997   Markle et al.
9,320,465 B2    4/2016   Kline
      (Continued)

OTHER PUBLICATIONS

Non-Final Office Action issue in U.S. Appl. No. 15/434,783 on Oct. 3, 2019.

(Continued)

*Primary Examiner* — Chu Chuan Liu
(74) *Attorney, Agent, or Firm* — Edwards Neils LLC; Jean C. Edwards, Esq.

(57)        ABSTRACT

The present invention relates to the process of using signal-emitting and/or receiving objects or smart medical devices for image acquisition, and which can utilize a variety of external energy sources which are directly applied and/or incorporated into the host subject to produce a continuous and dynamic visual representation of the host subject on a computer display, which representation hereafter will be referred to as a visualization map. The derived images can be targeted, to small (i.e., focal) areas of clinical interest, to organ systems, or the entire body. The present invention provides a scalable method for continuous and dynamic imaging over prolonged periods of time, as dictated by the clinical context.

25 Claims, 6 Drawing Sheets

Related U.S. Application Data a continuation-in-part of application No. 17/575,048, filed on Jan. 13, 2022, now Pat. No. 11,801,011, said application No. 17/712,693 is a continuation of application No. 16/503,920, filed on Jul. 5, 2019, now Pat. No. 11,324,451, which is a continuation-in-part of application No. 15/632,817, filed on Jun. 26, 2017, now abandoned, said application No. 17/575,048 is a continuation of application No. 15/434,783, filed on Feb. 16, 2017, now Pat. No. 11,224,382.

(60) Provisional application No. 62/694,248, filed on Jul. 5, 2018, provisional application No. 62/355,031, filed on Jun. 27, 2016, provisional application No. 62/295,787, filed on Feb. 16, 2016.

(51) Int. Cl.

| | | |
|---|---|---|
| *A61B 5/07* | (2006.01) | |
| *A61B 34/30* | (2016.01) | |
| *A61B 1/04* | (2006.01) | |
| *A61B 10/04* | (2006.01) | |
| *A61B 17/00* | (2006.01) | |
| *A61B 90/00* | (2016.01) | |

(52) U.S. Cl.
CPC ... *A61B 2034/303* (2016.02); *A61B 2090/365* (2016.02); *A61B 2090/3983* (2016.02); *A61B 2562/0285* (2013.01)

(56) References Cited

U.S. PATENT DOCUMENTS

| | | | |
|---|---|---|---|
| 9,895,103 | B2 | 2/2018 | Hyde et al. |
| 10,959,878 | B2 | 3/2021 | Wolfertz et al. |
| 2004/0034300 | A1 * | 2/2004 | Verard .................. A61B 90/36 |
| | | | 600/424 |
| 2010/0198048 | A1 | 8/2010 | Togawa |
| 2012/0035440 | A1 * | 2/2012 | Ferren .................. A61B 5/076 |
| | | | 600/302 |
| 2016/0029952 | A1 | 2/2016 | Hunter |
| 2017/0020422 | A1 | 1/2017 | Bigelow et al. |
| 2017/0068792 | A1 | 3/2017 | Reiner |
| 2017/0119278 | A1 | 5/2017 | Hyde et al. |
| 2018/0325618 | A1 | 11/2018 | Justin et al. |

OTHER PUBLICATIONS

Non-Final Office Action issue in U.S. Appl. No. 15/434,783 on Jul. 13, 2020.

Non-Final Office Action issue in U.S. Appl. No. 15/434,783 on Apr. 13, 2021.

K. Ogawa et al.; "On-chip internalization process of an intracellular nanobot into a single cell"; 2017 IEEE 30th International Conference on Micro Electro Mechanical Systems (MEMS); 2017, pp. 581-584, doi: 10.1109/MEMSYS.2017.7863473. (Year: 2017).

M. Pourhomayoun et al.; "Accurate Localization of In-Body Medical Implants Based on Spatial Sparsity"; IEEE Transactions on Biomedical Engineering, vol. 61, No. 2, pp. 590-597, Feb. 2014, doi: 10.1109/TBME.2013.2284271. (Year: 2014).

J. Li et al; Micro/nanorobots for biomedicine: Delivery, surgery, sensing, and detoxification. Science Robotics, 2(4), eaam6431; https://doi.org/10.1126/scirobotics.aam6431 (Year: 2017).

Non-Final Office Action issued in U.S. Appl. No. 16/503,920 on Oct. 7, 2021.

Non-Final Office Action issued in U.S. Appl. No. 18/362,616 on Sep. 11, 2025.

* cited by examiner

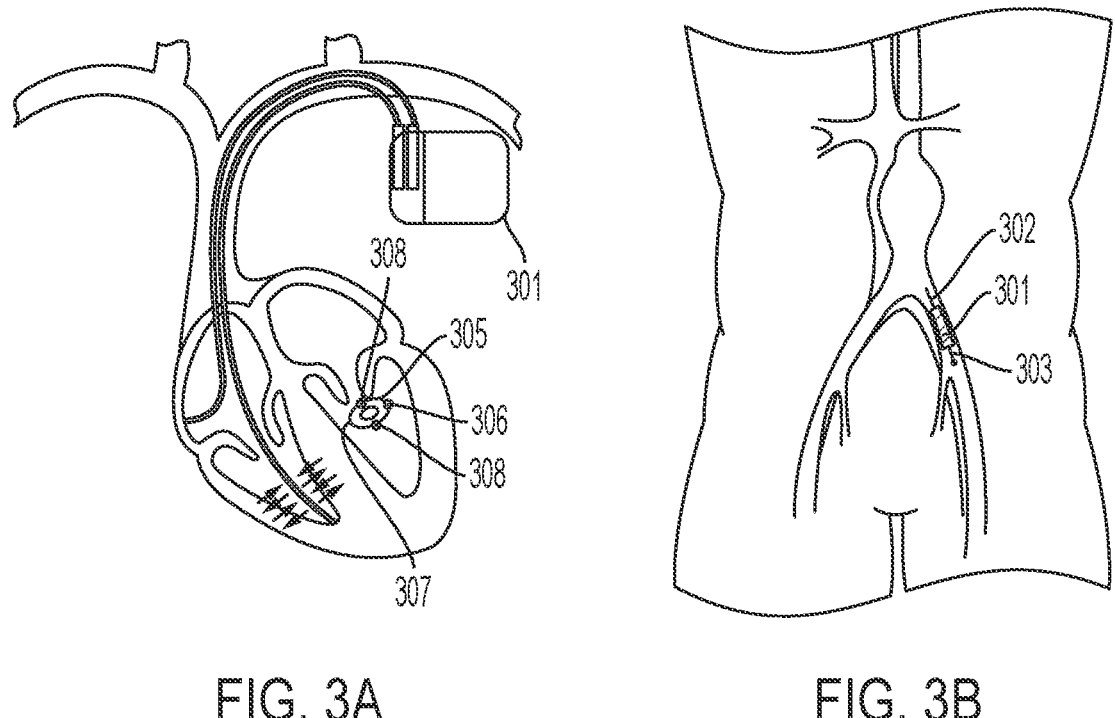
FIG. 3A
FIG. 3B
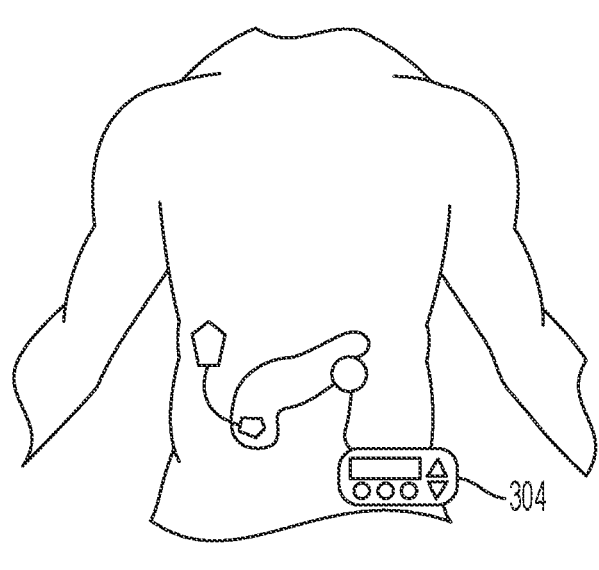
FIG. 3C

SIGNAL-EMITTING AND RECEIVING MEDICAL DEVICES WHICH PROVIDE DATA FOR REAL-TIME MULTI-DIMENSIONAL ANATOMIC VISUALIZATION MAPS

CROSS-REFERENCE TO RELATED APPLICATIONS

The present invention is a continuation-in-part (CIP) of U.S. patent application Ser. No. 17/712,693, filed Apr. 4, 2022, which is a continuation application of U.S. patent application Ser. No. 16/503,920 (the '920 Application), filed Jul. 5, 2019, now U.S. Pat. No. 11,324,451, which claims benefit of priority from U.S. Provisional Patent Application No. 62/694,248, filed Jul. 5, 2018, where the '920 Application is a CIP of U.S. patent application Ser. No. 15/632,817, filed Jun. 26, 2017, now abandoned, which claims benefit of priority of U.S. Nonprovisional Patent Application No. 62/355,031, filed Jun. 27, 2016, the contents of all of which are herein incorporated by reference in their entirety. The present invention is also a CIP of U.S. patent application Ser. No. 17/575,048, filed Jan. 13, 2022, which is a Continuation of U.S. patent application Ser. No. 15/434,783, filed Feb. 16, 2017, now U.S. Pat. No. 11,224,382, which claims priority from U.S. Provisional Patent Application No. 62/295,787, filed Feb. 16, 2016, the contents of all of which are herein incorporated by reference in their entirety.

BACKGROUND OF THE INVENTION

1. Field of the Invention

The present invention relates to a novel technology related to the process of using signal-emitting and/or receiving objects or smart medical devices for image acquisition, and which utilize a variety of external energy sources which are directly applied and/or incorporated into the host subject to produce a continuous and dynamic visual representation of the host subject, which hereafter will be referred to as a visualization map. The derived images can be targeted, to small (i.e., focal) areas of clinical interest, to organ systems, or the entire body. The present invention provides a scalable method for continuous and dynamic imaging over prolonged periods of time, as dictated by the clinical context.

2. Description of the Related Art

Conventional medical imaging involves a wide array of technologies which utilize different forms of energy for the creation of medical images. These include (but are not limited to) radiography, computer tomography (CT), nuclear medicine (e.g., positron emission tomography (PET)), ultrasound, and magnetic resonance imaging (MRI). Once these various forms of energy are applied to the host subject, the steps of image acquisition, image reconstruction and processing, and image computing are performed, resulting in 2 or 3-dimensional medical imaging datasets.

In the step of image acquisition, the energy applied may take a variety of forms, including (but not limited to) photons (radiography and CT), radioactive materials (nuclear medicine), radiofrequency signals from a magnetic field (MRI), or acoustic echoes (ultrasound). Regardless of the type of imaging modality, the data acquisition process includes conversion of the absorbed/modified energy into an electrical signal, preconditioning of the signal, and its digitization.

In the subsequent step of image reconstruction, mathematical algorithms are utilized to convert the acquired raw energy data into the form of an image. There are two primary classes of algorithms used for image reconstruction: analytical and iterative. Examples include filtered back projection in CT, Fourier transformation in MRI, delay and sum beamforming in ultrasound.

In the step of image computing, computational and mathematical methods are applied to the reconstructed imaging data to extract clinically relevant information. These methods include enhancement, analysis, and visualization.

Regardless of the specific imaging modality and energy source utilized, all existing medical imaging technologies lead to the creation of an imaging dataset which is static in nature, representing a single snapshot of the anatomy and pathology of the host subject at a specific point in time. As a result, if one wishes to evaluate changes in anatomy, physiology, and/or pathology over a given time period, repeated imaging acquisitions are required. The requirement to repeatedly acquire these images over a given time period results in additional cost, radiation exposure, time delays in diagnosis and treatment, and potential for iatrogenic complications.

In current practice, determination of anatomy (i.e., anatomic mapping) and medical device localization is performed using conventional medical imaging technologies including (but not limited to) radiography, computed tomography (CT), ultrasound, nuclear medicine, and magnetic resonance imaging (MRI). While these technologies continue to undergo incremental innovation, they do possess a number of practical limitations, which in large part are reflective of their static nature. In all of these technologies, medical images are created which capture a two (2)- or three (3)-dimensional imaging dataset which is essentially fixed (or static) at the time of image capture. As underlying conditions within the host patient inevitably change, repeat and/or additional imaging is required to update and redefine changes in anatomy and/or pathology.

Another deficiency of existing medical imaging technologies is the fact they are prone to a number of artifacts, perhaps the most important of which is motion. Since both voluntary and involuntary motion exists within the human body in a perpetual and ever-changing state, traditional anatomic imaging technologies are limited by the negative impact of motion on anatomic resolution, diagnostic accuracy, and clinical efficacy. As an example, when a three-dimensional (3D) cross-sectional computed tomography (CT) exam is performed for the purpose of localizing a vascular catheter, the CT can provide the generalized location of this catheter relative to a major blood vessel (e.g., superior vena cava) and/or internal organ (e.g., right atrium of the heart); but as the patient experiences physiologic (i.e., involuntary motion) over time due to vascular flow, respirations and cardiac motion, the relative position of this catheter constantly changes. While this change in location typically only amounts to a few millimeters or a few centimeters, this could prove to be clinically important when functionality is dependent upon precise localization (e.g., infusion of thrombolytic drug therapy).

Thus, a new way of producing continuous and dynamic visual representation of a host subject, over prolonged periods of time, where the derived images can be targeted to small (i.e., focal) areas of clinical interest, organ systems, or the entire body, is desired.

SUMMARY OF THE INVENTION

The present invention relates to a novel technology related to the process of using signal-emitting and/or receiving objects or smart medical devices for image acquisition, and which utilize a variety of external energy sources which are directly applied and/or incorporated into the host subject to produce a continuous and dynamic visual representation of the host subject, which hereafter will be referred to as a visualization map. The derived images can be targeted, to small (i.e., focal) areas of clinical interest, to organ systems, or the entire body. The present invention provides a scalable method for continuous and dynamic imaging over prolonged periods of time, as dictated by the clinical context.

The present invention utilizes smart medical devices with embedded biosensors and miniaturized smart devices (i.e., microbots, nanobots) of various functionality and composition (some of which are described in the above-identified U.S. patent application Ser. Nos. 17/712,693, 16/503,920, 15/632,817, 17/575,048, 15/434,783 and all the related applications (hereafter "the Incorporated Patents"), from which the present invention claims priority). These smart medical devices encompass every type of device, ranging in size and purpose, from the microscopic nanobots, to larger microbots, to miniature individual smart devices that include biosensors, and to larger medical devices such as pacemakers, catheters, endotracheal tubes, etc., which are outfitted as "smart devices" additional to their already intrinsic purposes. Herein, we will refer to these devices as "objects" or "smart devices" or "medical devices" interchangeably, and the exemplary embodiments may focus on a particular form of smart device, but one of ordinary skill in the art would know that these smart devices could encompass any device that has the apparatus and function described herein.

These smart devices provide a wide array of functionality and utility with regards to medical diagnosis, in vivo biodata collection, real-time analysis of both physiologic and pathologic states, co-mingling and analysis of biodata from multiple sources, therapeutic intervention, and real-time analytics.

In the present invention, the technology provides real-time and dynamic localization of these smart medical devices in vivo (which is defined as within a living organism). This ability to provide real-time and dynamic anatomic localization is a critical embellishment to smart devices, for it provides end-users with the ability to actively monitor smart device location and analyze its effect on physiology and underlying pathology in the performance of its clinical context.

An additional and novel application of the intervention is the ability to actively navigate smart device location, using the invention's anatomic localization capabilities and intrinsic mobility capabilities of the smart device. Collectively, these capabilities provide healthcare providers with the ability to dynamically assess host anatomy, smart device positioning, and offer proactive therapeutic intervention.

The present invention provides an entirely new technology for creation of real-time and dynamic anatomic localization, which can be applied to intrinsic host anatomy, pathology, and/or smart medical device positioning. This technology can be used to create an entirely new methodology for real-time dynamic 4-D anatomic visualization maps which have the potential to redefine medical imaging, diagnosis, and treatment.

In one embodiment, a system to create anatomic visualization maps of a body of a patient, includes: a medical device, having: at least one of a signal emitter which emits energy in a form of a transmitted signal, or a signal receiver which receives transmitted energy as a received signal, the signal receiver including at least one sensor or an antenna; a plurality of sensors and/or detectors; a passive or active propulsion mechanism; and an energy source; and an external signal receiver and/or transmitter which receives the transmitted signal; a controller which receives the transmitted signal from the external signal receiver and/or transmitter and converts the transmitted signal into a standardized form of data; and an external processor which receives the data and records the data in a database; wherein the external processor performs computational analysis on the data to produce a 4-dimensional (4D) anatomic visualization map of the body that is displayed on a display.

In one embodiment, the signal emitter emits energy in a form including at least one of chemical, electrical, radiant, sound, light, magnetic/magneto-inductive, mechanical, thermal, nuclear, motion, or elastic; and the transfer of the data is conducted by methods including at least one of near field communication (NFC), Bluetooth, infrared, microwave, Zigbee, satellite, light, or radio frequency (RF) transmission.

In one embodiment, the medical device is at least one of embedded in a patient or circulated within the patient in a localized anatomic region or systemically, throughout a body of the patient; and wherein the medical device is introduced into the body from one of a urinary bladder, lungs, bloodstream, skin, lymphatic system, or gastrointestinal tract.

In one embodiment, the medical device is one of a microbot, nanobot, miniaturized smart medical device, or other standard medical device including at least one of prosthesis, surgical hardware, or implant; and wherein on condition that the medical device is disposed in the body, the medical device is one of internally located and fixed or temporarily placed and/or transportable.

In one embodiment, the standard medical device is one of temporary or permanent in the body, the temporary medical device including at least one of vascular or bladder catheters, intravascular balloon pumps, drainage tubes, or short-term surgical hardware; and wherein the permanent medical device is at least one of vascular stents, pacemakers, infusion pumps, arthroplasties, prosthetic valves, or permanent surgical hardware.

In one embodiment, the external signal receiver and/or transmitter is embedded in an article of clothing or linens proximate to the body of the patient and the medical device and is accessed by the medical device via at least one of the data transfer methods.

In one embodiment, a plurality of medical devices is internally mapped by being positioned in proximity to one another internally in the body of the patient in a predetermined configuration.

In one embodiment, the medical device includes an internal processor; and at least one of the internal processor and/or the external processor determines a relative positioning of each medical device in relation to each other by analyzing metrics including at least one of distance, speed, or direction of travel of the transmitted signal, and thereby continuously updating the location of each medical device; and the computational analysis of the external processor includes a location of the medical device in 3-dimensional (3D) space which is achieved by one of triangulation or predetermined frequency of the transmitted signal.

In one embodiment, the medical device includes only signal emitters or signal receivers, or both signal emitters and signal receivers.

In one embodiment, the signal receiver of the medical device receives signals transmitted from at least one of the signal transmitters of other medical devices or from the external signal receiver and/or transmitter.

In one embodiment, one of a plurality of the medical devices or the external signal receiver and/or transmitter form a network, the plurality of medical devices forming a mesh network wherein each signal emitter of each medical device communicates only with other signal receivers of other medical devices and only one or more of the plurality of medical devices in the mesh network communicate with the controller.

In one embodiment the plurality of external signal receivers and/or transmitters form a relay of external signal receivers and/or transmitters.

In one embodiment, the transmitted signals received from the signal receivers are converted by the controller and/or the external processor into the 4D anatomic visualization map by at least one of spectroscopy, thermography, radiography and computer tomography, scintillators, magnetic resonance imaging (MRI), or ultrasound, and by at least one of iterative reconstruction, filtered back projection, convolutional neural networks, or Fourier transformation; and noise and measurement errors in the data are removed by filtering techniques by the external processor including at least Kalman filters.

In one embodiment, the 4D anatomic visualization maps are one of created by the user, or automatically created based on automated signal activations initiated by the external processor, at predetermined intervals or under predetermined conditions including movement of the medical device from a predetermined location; and the data is plotted over time by the external processor to create a dynamic 4D visualization map.

In one embodiment, the plurality of sensors and/or detectors includes at least one of biosensors, flow sensors, energy receptors, or distance sensors; and the distance sensors include at least one of ultrasonic, infrared, laser distance or time of flight light emitting diode (LED) sensors; and the distance sensors derive distance by measuring at least one of a time between signal transmission and receipt by the signal receiver of at least one of an intensity of the signal transmission or a pulse change; and the medical device navigates in the body based on a continuous feedback of transmitted signals to the signal receiver from other medical devices or the external transmitter/receiver, or from transmitted signals from within a target location.

In one embodiment, at least one of the internal processor or the external processor monitors a level of energy of the energy source, and on condition that the energy source falls to a predetermined threshold, the external processor initiates recharging of the energy source via the energy receptors, from external charging sources located at least one of internal or external to the body; and the energy source is at least one of a battery, biofuel cell, thermoelectricity, piezoelectric generator, photovoltaic cell, or ultrasonic transducer; and the external charging sources include at least one of light sources, electromagnetic fields, radiofrequency devices, ultrasound, thermal energy, sound, or vibration.

In one embodiment, on condition that charging of the energy source is indicated by the external processor, the medical device automatically seeks the energy source or receives instructions from the at least one of internal processor or the external processor to move to the energy source, and an automated alert is sent to a user that charging of the energy source is indicated.

In one embodiment, the microbots and nanobots are at least one of physically or coalesced with specific cell types in the body, or tagged to targets in the body including at least one of antibodies, circulating cells including at least one of macrophages, red blood cells, platelets, or lymphocytes, genetic material, bacteria, or tumor cells.

In one embodiment, the active propulsion mechanism includes a propulsion device activated by a propulsion activation mechanism to position the medical device, the propulsion device including at least one of chemically powered motors, enzymatically powered motors, external field driven motors, internally mounted miniaturized electrodes, miniaturized electromagnetic pumps, or appendages, activated by a propulsion activation mechanism.

In one embodiment, the transmitted signal is unique to each medical device and signal differentiation between a plurality of medical devices is accomplished by analysis of alteration in signal type, strength, direction, transmission time, frequency, or pattern.

In one embodiment, the 4D anatomic visualization map is created with other data sources in combination to produce a hybrid visual display, the other data sources including at least one of MRI spectroscopy, positron emission and computed tomography (PET-CT), or multispectral optoacoustic tomography.

In one embodiment, the medical device further includes: a reservoir and/or a tool disposed in a recess; and a deployment mechanism to deploy the tool from the recess; wherein the tool performs a plurality of actions including at least one of localized drug delivery, biopsy, microsurgery, thermal ablation, cryotherapy, embolization, or cauterization.

In one embodiment, the medical device is manually activated by user instruction, or automatically activated under predetermined conditions including at least one of damage to medical device structural integrity, achieving a predetermined threshold in energy source requiring charging, or manifestation of predetermined clinical conditions in the body of the patient; and an automated alert is sent to the user when the predetermined conditions are met.

In one embodiment, the transmitted signals are evaluated by the external processor for accuracy and reliability, and on condition that a transmitted signal is identified as not meeting predetermined standards of performance, or failure of the medical device to operate as required by the user, the medical device is instructed by the external processor to be at least one of moved to a predetermined location in the body for collection, turned off, destroyed, collected by another medical device, removed from the body as waste, or have the transmitted signal that fails to meet predetermined standards of performance ignored or bypassed by the external processor; and an automated alert is sent to the user that the medical device fails to meet the predetermined standards of performance.

Thus, has been outlined, some features consistent with the present invention in order that the detailed description thereof that follows may be better understood, and in order that the present contribution to the art may be better appreciated. There are, of course, additional features consistent with the present invention that will be described below, and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

BRIEF DESCRIPTION OF THE DRAWINGS

Exemplary embodiments of the present invention are depicted in the following drawings.

FIG. 3A shows a schematic internal view of the human heart with a cardiac lead and pacemaker signal emitter and/or receiver, and in another exemplary embodiment, a valve prosthesis with signal emitter and/or receiver, according to one embodiment consistent with the present invention.

FIG. 3B shows a schematic internal view of the left common ileac artery of the human body with an embedded object signal emitter and/or receiver, according to one embodiment consistent with the present invention.

FIG. 3C shows a schematic, partially internal view, with an artificial pancreas signal emitter and/or receiver, according to one embodiment consistent with the present invention.

DESCRIPTION OF THE INVENTION

Figure 1:
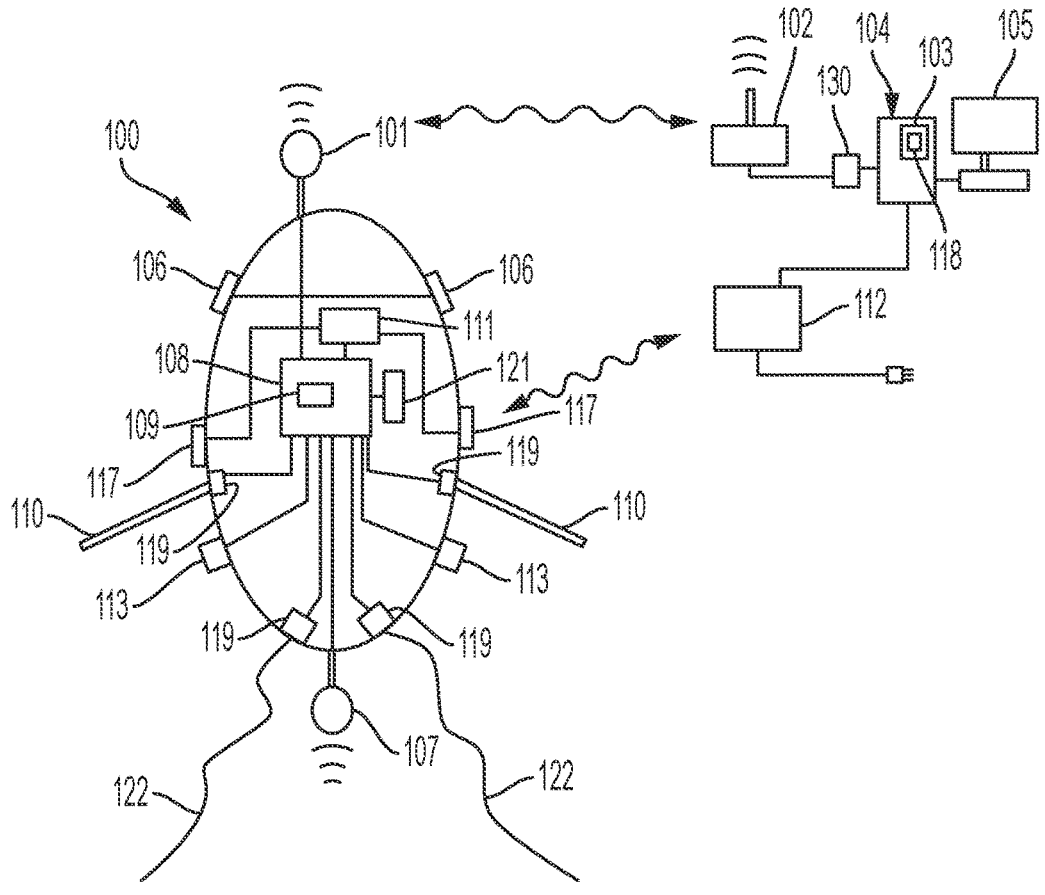
FIG. 1 shows a schematic drawing of the object signal emitter and/or receiver according to one embodiment consistent with the present invention.

The present invention relates to a novel technology related to the process of using signal-emitting and/or receiving objects or smart medical devices for image acquisition, and which can utilize a variety of external energy sources which are directly applied and/or incorporated into the host subject to produce a continuous and dynamic visual representation of the host subject on a computer display, which representation hereafter will be referred to as a visualization map. The derived images can be targeted, to small (i.e., focal) areas of clinical interest, to organ systems, or the entire body. The present invention provides a scalable method for continuous and dynamic imaging over prolonged periods of time, as dictated by the clinical context.

As noted above, the present invention utilizes smart medical devices with embedded biosensors and miniaturized smart devices (i.e., microbots, nanobots) of various functionality and composition (some of which are described in the above-identified U.S. patent application Ser. Nos. 16/503,920, 15/632,817, 17/575,048, 15/434,783 and their resulting patents (hereafter "the Incorporated Patents"), from which the present invention claims priority). These smart medical devices encompass every type of device, ranging in size and purpose, from the microscopic nanobots, to larger microbots, to miniature individual smart devices that include biosensors, and to larger medical devices such as pacemakers, catheters, endotracheal tubes, etc., which are outfitted as "smart devices" additional to their already intrinsic purposes. Herein, we will refer to these devices as "objects" or "smart devices" or "medical devices" interchangeably, and the exemplary embodiments may focus on a particular form of smart device, but one of ordinary skill in the art would know that these smart devices could encompass any device that has the apparatus and function described herein. Further, although the descriptions herein will focus on FIG. 1 in particular, one of ordinary skill in the art would know that the features shown in FIG. 1 could be applied to any smart device or object.

In one embodiment, the smart medical devices of the present invention contain microprocessors, data storages or memories, all run by computer program software, and are instructed externally from a computer system with microprocessor and/or controller, data storage or memory (or additionally, an external data storage), run by computer program software, connected to a display and keyboard with mouse for the user, etc., the computer system which is accessed by the smart medical devices by wireless methods as described in the Incorporated Patents.

In one embodiment, these smart devices provide a wide array of functionality and utility with regards to medical diagnosis, in vivo biodata collection, real-time analysis of both physiologic and pathologic states, co-mingling and analysis of biodata from multiple sources, therapeutic intervention, and real-time analytics.

In one embodiment, the present invention includes both internal and external anatomic localizing technologies, which collectively create one, two, three and/or four-dimensional (4D) anatomic visualization maps. The fourth dimension of these anatomic maps is provided by the capability of the invention to continuously modify and update the anatomic map over time, which takes into account the continuous voluntary and involuntary motion taking place in the host subject. Both attributes represent fundamental differences and upgrades to traditional anatomic localizing technologies.

In one embodiment, there are two principal components of the invention—objects 100 (and/or smart devices, and they shall be used interchangeably herein) which are signal emitters 101 or signal receivers (e.g., receivers 106, and/or antenna/receiver 107) or both (see FIG. 1 for examples of both in the same drawing, for simplicity of presentation). The objects and/or smart devices can be provided in a plurality of different structural embodiments, ranging in size and purpose such as those shown in FIGS. 1, 2C, 3A-3C and 4A-4B, as exemplary objects and/or smart devices 100, 206, 208, 300, 304, 308, 400 and 410, etc. However, one of ordinary skill in the art would know that any structural device which meets the requirements of design, function, operation, and mobility of the objects and/or smart devices of the present invention, could be envisaged. Further, hereafter, the objects and/or smart devices will be referred to generally as "objects 100", unless specific exemplary embodiments in the Figures are being described.

In one embodiment, the objects 100 function synergistically in a manner analogous to the image acquisition process in conventional medical imaging. In one embodiment, the object 100 signal emitters 101 can be embedded in or circulate through the host (i.e., patient) and emit energy in the form of a signal (i.e., wireless), which in turn is captured and recorded by a corresponding external signal receiver 102 (see FIG. 1) outside of the body (or, in another embodiment, by an internal object signal receiver 106/107 within the body as described below).

Figure 2A:
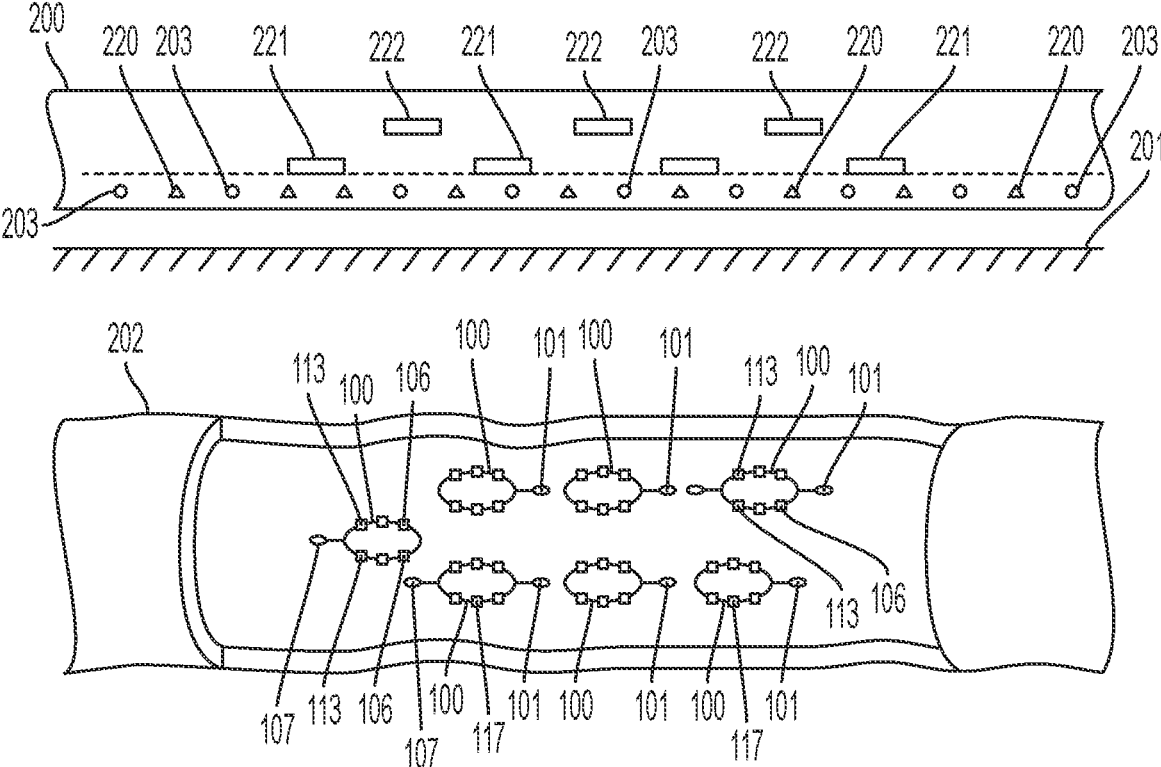
FIG. 2A shows a side schematic, partial internal view, of a blood vessel within the human body containing the signal emitting and/or receiving objects and shows a charging device such as embedded charging elements provided in clothing, for external charging of the objects, according to one embodiment consistent with the present invention.
Figure 2B:
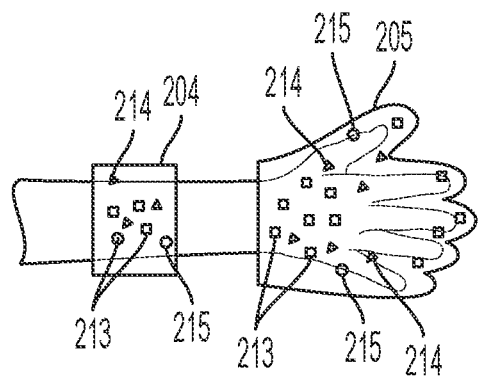
FIG. 2B shows a top view of a hand of a human being with two exemplary embodiments of the present invention, namely a wristband and a glove (or other external materials or linens) each containing object signal emitters and/or receivers, and sensors, and which can provide external charging for internal object signal emitters and/or receivers or smart devices using external charging sources in the wristband or glove, according to one embodiment consistent with the present invention.
Figure 2C:
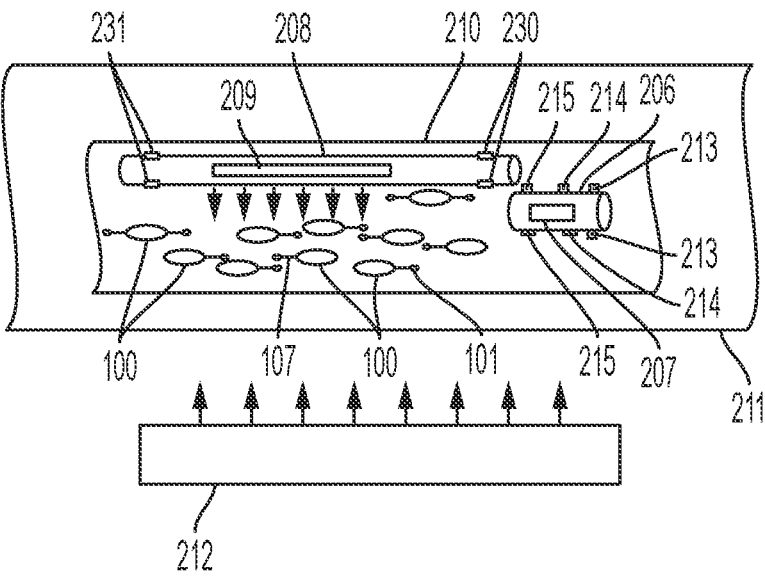
FIG. 2C shows a side schematic, partial internal view, of a blood vessel within the human body containing the object signal emitters and/or receivers, which receives external charging from an internal charging device or source, such as a catheter with embedded charging source, or alternatively, an external charging source such as a light source or electromagnetic source, according to one embodiment consistent with the present invention.
Figure 4A:
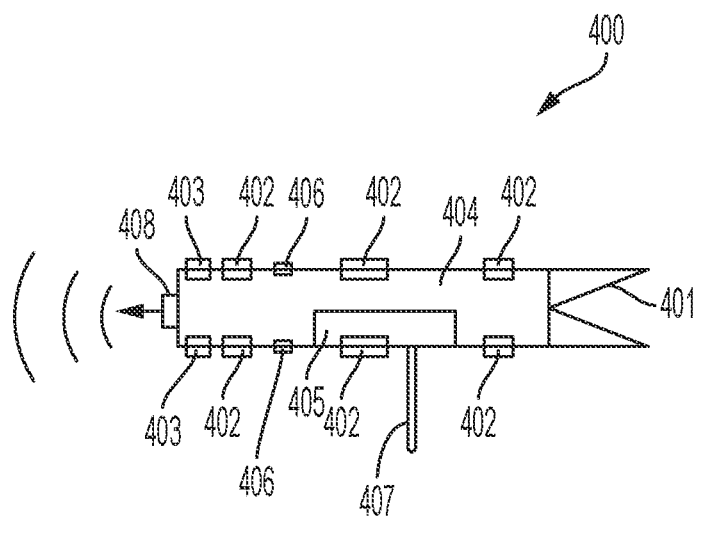
FIG. 4A shows a schematic, internal view, of an object/smart device with signal emitters and/or receivers, and sensors, with one embodiment of a cutting tool at one end, a propulsion mechanism at the other end, and one embodiment of an tool that can be extended from within the object and retracted back into the object, such as a needle, and an internal space including a reservoir, according to one embodiment consistent with the present invention.
Figure 4B:
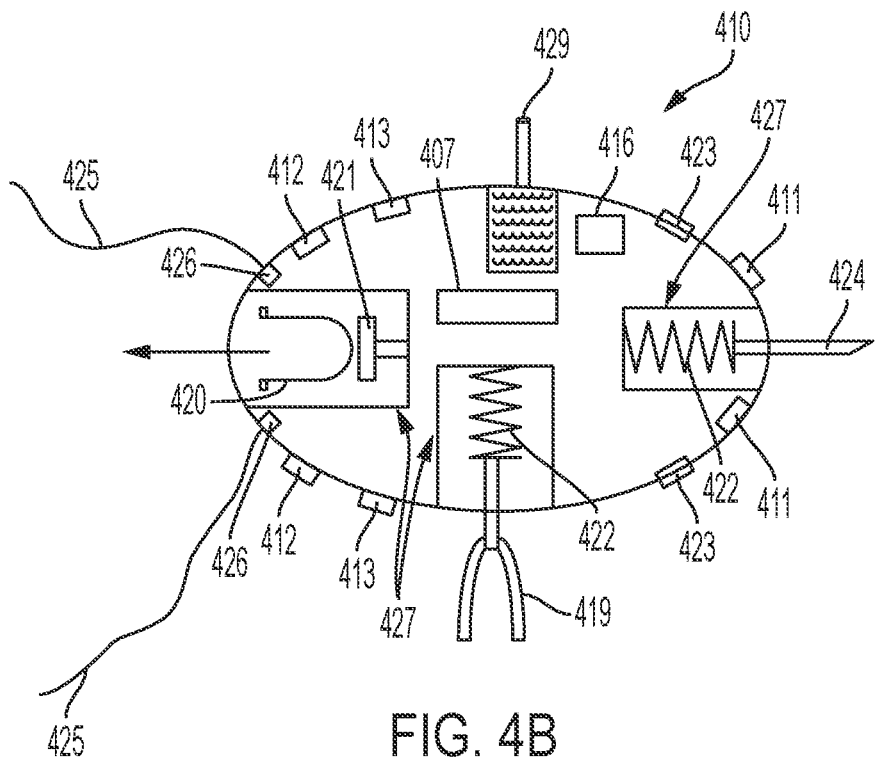
FIG. 4B shows a schematic, internal view, of an object signal emitter and/or receiver, with sensors, a cauterizing tool at one end and a clip at another end, with an attachment tool on the side, as exemplary tools that can be released from internal spaces within the object, and returned inside the object, by exemplary means of springs and rods; and an exemplary propulsion device.

Note that, in one embodiment, the external signal receiver 102, as shown in FIG. 1, is a specific, dedicated receiver 102 which communicates with a computer system 104; however, the external signal receiver can be a variety of structural embodiments, including clothing or linens (e.g., clothing or blanket 200 in FIG. 2A), accessories (e.g., wristband 204, glove 205, in FIG. 2B), medical devices—either internal (e.g., object 100 in FIG. 2C, pacemaker 300 in FIG. 3A, valve prosthesis 308 in FIG. 3A, catheter 208 in FIG. 2C) or external (e.g., pancreatic control device 304, in FIG. 3C), or other types of external receivers.

In one embodiment, once the external signal receiver 102 wirelessly receives the signal, it is forwarded to a controller 130 (which makes sense of the signals coming into and going out of the computer system 104), by cable or wirelessly, where the signal energy subsequently undergoes analysis by a computer processor 103 (see Incorporated Patents for detailed description of the computer system 104), in order to determine the exact location of the signal transmitter 101 in 3-dimensional (3D) space. With the collection of extremely large numbers of signals (i.e., thousands, millions), computerized processing by the microprocessor 103 and data analysis by the program, will eventually lead to the production of anatomic visualization maps created by the program, which are provided to the user on display 105.

In one embodiment, the signal emitters 101 are disposed on miniaturized objects 100 which are imbedded in or circulate through the host body and can take a variety of forms including (but not limited to) biologically inert particles, compounds, and/or devices (e.g., microbots, nanobots—see the Incorporated Patents). FIG. 1 provides one non-limiting example of such an object 100 with signal emitter 101. In one embodiment, the object 100 with signal emitter 101 emits various types of energy including (but not limited to) chemical, electrical, radiant, sound, light, magnetic/magneto-inductive, mechanical, thermal, nuclear, motion, and elastic.

In one embodiment, the object 100 with signal emitter 101 can be introduced to the host in a variety of ways, with the purpose of being embedded in or circulating within a localized anatomic region or systemically, throughout the entire body. Examples of local introduction, but not limited to these, include the urinary bladder (through a Foley catheter), the lungs (through inhalation), the bloodstream (by injection, catheter), the skin (dermal patch) and the gastrointestinal tract (through ingestion).

More specifically, in exemplary embodiments, generalized object signal emitter 101 distribution occurs through the bloodstream via intravenous injection, or deployment through medical devices such as an intravascular catheter 208 (see FIG. 2C), or absorption via the GI tract after ingestion, or other suitable method. In addition, objects 100 with signal emitters 101 can also be delivered superficially though a dermal delivery mechanism like a patch and subsequently enter the host bloodstream through absorption. Another generalized distribution system includes insertion into the lymphatic system, which like the bloodstream, circulates through the entire body.

In one embodiment, generally speaking (and focusing on FIG. 1 as an exemplary embodiment), once the object 100 signal emitter 101 enters the host subject and begins circulation, it emits energy in the form of a signal, which in turn is captured by a corresponding external signal receiver 102 (or internally, by another object 100 signal receiver 106/107). When the signal is received by external signal receiver 102, the receiver 102 captures the transmitted energy and the controller 120 converts this into a standardized form of data (see Incorporated Patents for more description of the computer system 104), which in turn is recorded by the computer program in a database in memory 118 of the microprocessor 103, and the data undergoes computational analysis by the program.

In one embodiment, energy capture can also be performed by miniaturized sensors and/or detectors 106 (vs. antennas 107 etc.), which are embedded within objects 100 and act as signal receivers 106/107. The objects 100 with signal receivers 106/107 can take a variety of forms, which in part are dependent upon their location. When located externally, size restrictions are less stringent. But when internally located (i.e., inside of the host), signal receivers 106/107 must be extremely small in size, as in the case with objects 100 which are microbots or nanobots.

In one embodiment, the transfer of the emitted signals from object 100 signal emitter 101 and their associated data takes place in a standardized fashion, so that the combination of signal emission, transfer, and receipt occurs in a reproducible and consistent fashion. One (but not the only) way to accomplish this data transfer is through near field communication (NFC), which is a standardized mechanism for two-directional data exchange using short distance radio waves. NFC requires a relatively small distance at this time (approximately 10 cm), but this distance will be increased with future technological development. Thus, for the most part, the (external) signal receivers 102 are positioned at short distances from the object 100 signal emitters 101. Other techniques for signal transfer include Bluetooth, light, and RF transmission, which extend much further distances.

In one embodiment, one way to accomplish the transfer and receipt of emitted signals from the objects 100 is to create a superficial network of external signal receivers 102, which will satisfy the distance requirements when the object 100 transmitters 101 have limited range such as with NFC. In one exemplary embodiment, clothing 200 (see FIG. 2A) or other superficial materials with embedded signal receivers 203 which can be positioned over the anatomic region 201 of particular interest, proximate to the location of the objects 100 in the blood vessel 202, for example. The emitted signals are then received by the superficial receivers 203 and the resulting data analyzed by the program. However, with improved distances, the signal receivers 102 can be placed anywhere in a home or office, for example, and can be accessed from anywhere via wireless transmission methods.

In one embodiment, as the emission signals are recorded by the program in the memory 118 of the processor 103 of the computer system 104 (or external memory), the superficially positioned signal receivers 102, are then analyzed by the program using various program modules of the processor 103 (i.e., navigation module, GPS locator, frequency detector module, etc. (see Incorporated Patents)) to detect the location of the object 100 signal emitter 101 in 3-D space. In one embodiment, using triangulation, the program analyzes the signals received by the signal receivers 102 based on signal strength and directionality to locate the point of origin and distance from the location of the sensor and/or detector 106 which is receiving the signal. In other methods, the particular frequency or other technological methods can identify the object 100 signal emitter 101.

In another embodiment of the present invention, the object 100 signal emitters 101 and signal receivers 106/107 can be positioned in proximity to one another and positioned internally within the host body in a predetermined configuration (which will be subsequently referred to as internal mapping). As an example, suppose miniaturized microbots or nanobots 100 are injected into the bloodstream of a host subject for the purpose of creating a comprehensive visualization map of the present invention. These miniaturized bots 100 have the capability of being strictly signal emitters 101, strictly signal receivers 106/107, or both emitters 101 and receivers 106/107 (i.e., dual purpose). In this setting, the signal emitters 101 and signal receivers 106/107 are physically located alongside one another (see FIG. 2A), which creates a number of practical and theoretical advantages including (but not limited to) a large sample size of signals for analysis, lower energy requirement for signal emission, and diminished potential for background noise and/or distortion of the signals received (due to less signal distance travelled).

In this embodiment where the signal receivers 106 are internally located, the sensors 106 they contain will be continuously receiving and processing signals emitted by their other object 100 signal emitter 101 counterparts. The signals received or emitted by the objects 100 can be processed internally using a controller 121 and microprocessor 108 having an internal memory 109, and a software program which can direct object 100 operations.

In one embodiment, as neighboring object 100 signal emitters 101 and receivers 106/107 travel and continuously process the corresponding signals (see FIG. 2A, for example), their relative positioning to one another will be continuously updated by program run by the external or internal microprocessor 103, 108 and defined, along with metrics determined by the program, such as distance, speed, and direction of signal travel. All this information is provided back in the way of signals via controller 121 to the external computer system processor 103 for analysis. Any change to the positioning can be provided back from computer system 104 to the objects 100 via signals intercepted by the receivers 106/107, and/or by internal instructions from object 100 microprocessor 108 to propulsion device 110 via propulsion activation mechanism 119 (e.g., arms 110 activated by motor 119).

In one embodiment, with the program plotting this data over time, the program can create a dynamic visualization map. The combination of objects 100 as transmitters 101 and/or receivers 106/107 can also form the equivalent of a "mesh" network whereby each transmitter 101 does not necessarily need to communicate with an outside sensor 102 but instead can communicate with other receivers/transmitters 106/107/101; and one or more objects 100 of the network forwards signal information to external receivers 102 and the processor 103.

In one embodiment, the methods for signal receiving from the objects 100 and conversion of these signals into an anatomic map by the program can utilize a variety of technologies, including (but are not limited to) spectroscopy (chemical signals), thermography (thermal signals), radiography and computer tomography (radiation signals), scintillators (nuclear signals), magnetic resonance imaging (MRI) (electromagnetic signals), and ultrasound (sound signals). In one embodiment, the methodology for the program to convert the signal data into anatomic visualization maps is performed with a variety of data processing techniques including (but not limited to) iterative reconstruction, filtered back projection, convolutional neural networks, and Fourier transformation.

In one embodiment, by using a variety of algorithmic filtering techniques (e.g., Kalman filters) used by the microprocessor 103, the program can improve localization and mapping with removal of noise and measurement errors from the data. The resulting maps produced by the program contain a variety of space measurements and visualization maps which include (but are not limited to) free space, obstacles, and unexplored space. When applying this principle to the invention and the human body, the maps created by the program can contain normal tissue anatomy, pathology, points of relative obstruction, and open circulation (e.g., blood steam, lymphatics, respiratory airways).

In one embodiment, the quality of the maps generated by the program is in large part determined by the quality and number of signals transmitted to and received by the objects 100, along with the derived data, computational analysis, and determination and correction of data inaccuracies by the program. By using large numbers of object 100 signal emitters 101 and receivers 106/107 in the form of microbots and nanobots 100, which travel in close proximity to one another (see FIG. 2A), one could dramatically increase the sample size and accuracy of the sensor 106 derived data. This would lead to the creation of high-resolution visualization maps by the program, which are continuously updated and refined (i.e., self-corrected) by the program, while simultaneously demonstrating subtle changes over time (i.e., dynamic visualization).

In one embodiment, the principles regarding using simultaneous localization and 3-D mapping using mobile sensors contained within robots moving within a given area, on a large scale, can be readily applied to miniaturized bots 100 (microbots and nanobots) containing sensors and/or detectors 106 moving within the human body. Existing innovation efforts have developed an entirely new category of sensors 106 which enable communication at the nanoscale level using magnetic dynamic fields. As innovation continues to reduce the size of bots, sensors, detectors, and processing units; the practicality and functionality of the present invention will continually expand.

In the specific internal embodiment of the invention, the distance between circulating object 100 signal emitters 101 and receivers 106/107 can be determined through the incorporation of sensors 113 (i.e., distance sensors 113), which can derive distance by the program of the microprocessor 108 determining the following measurements:

1. Time between signal emission and receipt.

2. Intensity of the signal.

3. Phase change (between signal emitted and received).

In one embodiment, a number of different types of distance sensors 113 exist, including (but not limited to) ultrasonic, infrared, and laser distance (LIDAR), and time of flight LED sensors.

In one embodiment, in addition to circulating object 100 signal emitters 100 and/or transmitters 106/107, internally located fixed object 100 signal emitters 101 and/or signal receivers 106/107 are also possible. Examples may include (but are not limited to) internally positioned devices such as prostheses (e.g., prosthetic heart valve 305 (see FIG. 3A)), surgical hardware, traditional or standard medical devices (e.g., cardiac pacemaker 300—see FIG. 3A), implants, or other smart devices 301 with emitters 302 and/or sensors/receivers 303 (see FIB. 3B). By embedding objects 301 (see FIG. 3B) having signal emitters 302 and/or sensors or receivers 303 within the physical structure of these devices 301, a continuous source of signal emission/receiving is available, which can be activated as needed. In addition, the relatively fixed anatomic location of these devices provides for accurate signal localization in 3-D space.

In one embodiment, the objects 100 with internal signal emitters 101 and/or receivers 106/107 can be temporarily placed—i.e., they are fixed in location at any single point in time but readily transportable.

Regardless of the individual type or location of the objects 100, the general functionality remains the same. As object 100 signal emitters 101 and/or receivers 106/107 transmit signals, energy is emitted and detected, which in turn generates data for localization of the signal emitters 101 in 3-dimensional space, and the creation of 4-D visualization maps by the program.

In one embodiment, unlike most conventional medical imaging technologies, the present invention provides the ability to demonstrate temporal change in anatomy and its positioning. The slight variations in this real-time and dynamic anatomic display can provide important anatomic and physiologic data as to voluntary and involuntary motion, which is important in accounting for minute changes in anatomic positioning. As an example, if one wishes to create a 4-D anatomic display map of the coronary arteries, one would need to account for the constant physiologic motion of the heart, as it changes during the cycles of systole (i.e., ventricular contraction) and diastole (i.e., ventricular relaxation). The corresponding anatomic display map created by the program would provide visualization of the coronary arteries and the small changes in location experienced during respiration, patient movement, and the different phases of the cardiac cycle.

In one embodiment, in addition to the anatomic changes which occur through temporal change and motion, pathology can also change. In the example of the coronary arteries, anatomic variability occurs with involuntary and voluntary motion. But the same can take place with pathology. A diseased right coronary artery may exhibit 50% stenosis during systole, which increases to 65% during diastole. The ability to detect subtle, yet important changes in pathology over time due to physiologic change is an important attribute of the present invention, which does not exist in a comparable way with conventional imaging modalities.

In one embodiment, an important feature of the present invention is the ability of the program to perform longer term temporal change analysis. The usual application of the present invention just described refers to evaluation of subtle change which occurs over a short time period (i.e., seconds). However, the present invention also provides the ability to expand anatomic visualization mapping over a much longer period of time (i.e., minutes, hours, even days). During the service of the object 100, the microprocessor 108 monitors the level of energy in the internal energy source 111, and upon reaching (falling to) a predetermined threshold, the program will initiate recharging via energy receptors 117, which can receive energy externally transmitted to the object 100 from external charging sources 112 (or source 212 in FIG. 2C, for example). As the lifetime of the object 100 signal emitters 101 and/or signal receivers 106/107 is extended by technologies that permit this recharging of internal energy sources 111 via external charging devices 112, and thus, longer energy life expectancy, then continuous and prolonged signal capture and analysis by the program will occur, providing the ability of the program to continuously visualize anatomy and pathology over these expanded time periods.

In one embodiment, as a result of this expanded temporal analysis by the program, computerized analysis (e.g., temporal subtraction) by the program can render a number of visualization maps, including a map which shows what is termed "maximum change". The changes highlighted by the program in this temporal subtraction map can visualize changes in anatomy and pathology over the entire period of signal analysis—i.e., "maximum change". In the earlier example of the coronary artery stenosis which showed incremental change during the cardiac cycle, suppose that over a two-hour period of imaging analysis, the patient experienced a transient cardiac arrythmia (e.g., atrial fibrillation), which lasted for a 30-second period and was relatively asymptomatic. However, during this 30-second time period, the visualization map created by the program is able to demonstrate several substantive changes from baseline including change in the cardiac rate and rhythm, diminished left ventricular ejection fraction, and interval worsening in the measured coronary artery flow. Thus, unlike existing medical imaging technologies which are static and fixed over time, the dynamic and continuous nature of the present invention provides for longitudinal analysis of anatomy and pathology along with the ability of the program to time stamp the changes which occur.

In one embodiment, one net result is that the anatomic visualization maps created by the program, which are dynamic in nature, provide a novel method for detecting change and variability in both anatomy and pathology. Another benefit derived from the present invention is the program's ability to quantify pathology in both form and function. Since the sensors 106 are capable of deriving flow velocity measurements (i.e., the program can perform measurements of the time required for object 100 signal emitters 101 and receivers 106/107 to travel over a defined distance), the same coronary artery stenosis can be defined by the program both in area and velocity measurements. At the same time, when collateral pathways for coronary flow are established due to critical stenosis, the program can take the resulting data, allowing the program to define anatomic and physiologic change by displaying on a display 105, the native coronary arteries, collateral vessels, and the velocity flow measurements in the full complement of vessels for user review.

In one embodiment, a primary (but not exclusive) route of distribution of the objects 100 would be the bloodstream and/or lymphatics since these systems are systemic, supplying the entire host body. In certain situations, alternative organ systems may be selected by the user (or the program, if designated) as the primary site for object 100 signal emitter 101 and/or receiver 106/107 distribution. As an example, if the user wants to selectively display on the display 105, a 4-D anatomic map of the respiratory system created by the program, the user may opt to introduce and distribute the object 100 signal emitters 101 and/or receivers 106/107 exclusively within the tracheobronchial tree by delivering the objects 100 directly into the trachea (which is the major site of air inflow) through inhalation or an aerosolized spray. The object 100 signal emitters 101 and/or receivers 106/107 in this example would subsequently become distributed throughout the respiratory system through air currents, resulting in the program being able to create a 4-D map exclusive to the respiratory system and underlying lung anatomy based on the resulting data received.

In one exemplary embodiment where this targeted approach may be beneficial would be in the setting of lung cancer, where a relatively small focus of pathology (e.g., 10 mm) resides in a peripheral location of the lung. In this scenario, the object 100 signal emitters 101 can be delivered through inhalation or injected into the bloodstream and go on to become distributed throughout the entire respiratory tract. The resulting 4-D anatomic map created by the program would display on a display or monitor 105, all relevant anatomy contained within the lungs on a macroscopic level, including but not limited to lung architecture, blood vessels, lymphatics, soft tissues, and lymph nodes.

In one embodiment, in addition to the macroscopic visualization maps described, the present invention also offers the unique opportunity for the program to create visualization maps on a cellular (i.e., microscopic) level. This becomes possible as nanobots 100 become the primary vehicle for signal emission and/or receiving. Due to their small size (in micrometers), nanobots 100 are the size equivalent of biological cells, and as such, have the potential to define anatomy and pathology on a cellular level.

In one embodiment, the circulating microbot and nanobot 100 signal emitters 101 and/or receivers 106/107 can circulate and become positioned within a small foci of pathology (e.g., infection, malignancy, inflammation). In addition to freely circulating in an unencumbered state, the microbots and nanobots 100 can also be physically tied and/or directed by the program to move and coalesce with specific cell types (e.g., white blood cells), which provide a mechanism for cellular aggregation. This expands the functionality of microbots and nanobots 100 for the program to display, map, and quantify pathology in a dynamic fashion on both macroscopic and microscopic levels on the display 105.

In one exemplary embodiment, white blood cell tagging to the microbots or nanobots 100 with radioactive indium-111, provides for nuclear medicine imaging (i.e., scintigraphy), such that anatomic/pathologic visualization maps could be created by the program, the visualization maps which are exponentially superior in anatomic resolution, provide dynamic visualization of pathologic change, and provide functional analysis on both macroscopic and microscopic levels.

In one embodiment, in addition to white blood cells, a wide array of other macroscopic and microscopic tagging targets can be utilized with the present invention. Examples include (but are not limited to) antibodies, other circulating cell types (e.g., macrophages, red blood cells, platelets, lymphocytes), genetic material (i.e., RNA, DNA, genes), bacteria, and tumor cells. The principal advantage of utilizing such tagging agents is for the program to provide functional analysis of pathology, along with the inherent structural analysis of pathology.

In one embodiment, targeted object 100 signal emitter 101 and/or receiver 106/107 distribution can occur within any organ system, with the signal emitters 101 and/or signal receivers 106/107 introduced by either passive or invasive techniques as described above. As previously mentioned, representative examples of passive techniques include the gastrointestinal and respiratory tracts (where signal emitters are introduced though ingestion and inhalation respectively). Representative examples of invasive delivery may occur through the introduction of catheters or needles, which are positioned within a specific organ entry site. Non-limiting examples include Foley catheter within the bladder, nephrostomy tube in the kidneys, lumbar puncture within the subarachnoid space and cerebrospinal fluid, injection into the peritoneal cavity with ascites (i.e., intraperitoneal fluid), and intraarticular injection within a given joint space (e.g., knee, hip).

In one embodiment, the manner in which object 100 signal emitters 101 and/or receivers 106/107 migrate can be passive or active. Passive migration and distribution are when the objects 100 have no intrinsic capability of self-propulsion (i.e., arms 110) and as a result are transported passively by the intrinsic current of the medium in which they are localized. Examples include (but are not limited to) the bloodstream, airways, cerebrospinal fluid, and gastrointestinal tract. Alternatively, active transport can occur when the object 100 signal emitters 101 and/or receivers 106/107 are capable of propulsion. Mechanisms for self-propulsion of microbots and nanobots 100 include (but are not limited to) chemically powered motors (e.g., hydrogen peroxide), enzymatically powered motors (e.g., urease and glucose oxidase), external field driven motors 408 (see FIG. 4A) (e.g., magnetic, light, ultrasound), internally mounted miniaturized electrodes, miniaturized electromagnetic pumps, and appendages (e.g., side-to-side movement of tails, whip-like tails 122, small arms 110, (both tails 122 and arms 110 shown in FIG. 1 for convenience), etc.).

Since internal energy sources 111 are limited by size constraints, in one embodiment, the present invention includes a unique approach to provide external energy sources 112 to power the microbots and nanobots 100. When an external energy source 112 is utilized, the charging signal is picked up by energy receptors 117 on the objects 100, and the circulating lifetime of the object 100 signal emitters 101 and/or receivers 106/107 can be dramatically enhanced (i.e., hours, days), which can allow for the creation of dynamic anatomic visualization maps by the program over prolonged time periods. This can be especially helpful when evaluating pathologic states which can significantly change or evolve over time such as stroke, heart attack, active bleeding, and aggressive infection. Having a continuous dynamic and real-time method for ongoing anatomic/pathologic assessment can prove extremely valuable in time sensitive situations and potentially make the difference between life and death.

The ability of the program of the present invention to provide long duration visualization maps also provides a method with which anatomy and pathology can be actively evaluated pre- and post-intervention. As an example, suppose a patient has incurred post-traumatic injury and active bleeding to the kidney. The ability of the program to dynamically image and display (on display 105) the kidney over time presents a non-invasive method for monitoring change in size and extent of renal injury and bleeding, as well as quantify the rate of active bleeding. If, arterial embolization is selected by the user (or by the program) as the treatment of choice in lieu of surgery, continuous visualization maps can be provided by the program before, during, and after the embolization takes place; actively evaluating treatment response as well as potential iatrogenic complications (e.g., renal infarction).

Another example of pathology defined by abnormal flow of circulating microbots or nanobots 100 is when an abnormal pathway is created between normal anatomic structures, which is called a fistula. The visualization map created by the program of the present invention will not only visualize and localize the abnormal pathway (on display 105) but also quantify its measurements and flow characteristics on the display for the user.

In one exemplary embodiment, a pathologic fistula would be a bronchopleural fistula which is an abnormal pathway connecting a distal airway (i.e., bronchus) with the pleural space (i.e., potential space outside of the lung). When such a fistula is created, the abnormal pathway results in air from the bronchus abnormally collecting within the pleural space, creating a pneumothorax which can collapse the normal lung and become life threatening. However, in operation, the object 100 signal emitters 101 and/or receivers 106/107 circulating through the lung will not only display normal lung anatomy but also display the abnormal fistulous tract, as objects 100 pass from the distal bronchus into the pleural space. This allows the program to provide a detailed anatomic map of the fistula, along with the underlying dynamics of abnormal airflow within the fistula, which would not be readily available through conventional anatomic displays.

In one embodiment, in the event that treatment was to occur aimed at closing this abnormal fistulous tract, the visualization map created by the program can show both structural change in the fistula as well as flow changes. Quantitative measurements taken by the smart devices, microbots and nanobots 100, such as flow rate and volume within the fistula, can provide important clinical information which the program can analyze to create to treatment response and determination of alternative treatment requirements for the user.

Returning to the subject of energy sources for microbot and nanobot 100, the present invention includes a number of potential external energy sources, including (but not limited to) light sources 212, electromagnetic fields, radiofrequency devices, ultrasound, thermal energy, sound, and vibration. These sources can serve as effective charging stations (e.g., charging station 112), which can be likened to a cell phone charging station. Energy can be transferred from the external power source 112 to the circulating objects 100 when the internal power source 111 of the objects 100 (i.e., microbots, nanobots, smart devices) are below a predetermined level. In that event, the objects 100 will automatically seek a charging station 112 in a variety of ways, not limited to wirelessly seeking the charging source 112, or moving to a position in the body where the charging source (e.g., internal catheter charging source 209, external light charging source 212) is positioned. In one embodiment, the drop below a predetermined charging level triggers a signal to the processor 103, and the program then provides an alert to the user that a charging station 112 (or charging source 112, etc.) is required. The alert is usually sent by electronic methods—i.e., email, text, fax, or screen alert, etc. The charge obtained will effectively replenish the objects' 100 internal energy and extend their lifetime.

In one embodiment, a variety of power sources (i.e., object internal energy source 111, or external energy sources 112, 209, 212) can be used to propel the medical device 100—including (but not limited to) batteries, biofuel cells, thermoelectricity, piezoelectric generators, photovoltaic cells, and ultrasonic transducers. As advances in micro and nanotechnology continue, the range of possibilities for power supply will continue to expand, along with decreasing physical size requirements of the components. The net result is that miniaturized power supplies can be directly incorporated into smart medical devices 100 and provide for in vivo medical device propulsion and navigation.

In one embodiment, administering external energy to the circulating objects 100 is through superficial placement of the charging device 112, 212 on the outside of the host (e.g., external energy source 212, wristband energy source 204, glove energy source 205, garment energy source, belt, necklace, shoes, socks, glasses, etc.) (see FIGS. 2B-2C). As the energy is emitted, the circulating objects 100 along its path can absorb the transferred energy. Since all circulating objects 100 will ultimately pass in close proximity to the charging device (i.e., external charging sources 112, 212, 204, 205 etc.), the energy delivered will reach all circulating objects 100. In those circumstances, where the visualization map produced by the program is limited to a focal area of anatomy (e.g., heart), the charging device (light source 212 etc.) can be strategically positioned directly over the anatomic region of interest.

In one embodiment, one could also employ an object 100 such as a smart device 206 (see FIG. 2C), as an internal charging agent, by embedding the charging mechanism 207 directly into the device 100 and remotely controlling its on/off function. In another embodiment, another device such as a vascular catheter 208 (see FIG. 2C), with an embedded charging mechanism 209, could be inserted into a blood vessel 210 in the body 211 and moved proximate to the objects 100 in need of charging, by using its own signal emitters 230 and receivers 231 to receive navigational instructions (using an internal processor etc.), and/or by user action based on visualization on the display 105.

In one embodiment, since the number of objects 100 can be extremely large (millions or even billions), a unique signature may be required to differentiate one object 100 from another. This signal differentiation can be accomplished in a variety of ways including (but not limited to) alteration in signal type, frequency, or pattern.

In one embodiment, if the signals being emitted by the objects 100 are unique and specific to each circulating object 100 signal emitter 101, then other object 100 signal receivers 106/107 and their embedded sensors 106 can determine signal strength, direction, and transmission time specific to each individual signal emitter 101. When a given signal emission is received by multiple object 100 signal receivers 106/107, triangulation can be used by the program of the object 100 processor 108 (or externally by the program of processor 103) to determine the exact location of the object 100 signal emitter 101 at the time of signal transfer. At the same time, this same object 100 signal emitter 101 is continuously moving, so continuous positional changes are calculated by the program (by either or both internal and/or external processors 108, 103—referred to as "the program") based on triangulation of each individual object 100 signal transmission. The dynamic nature of continuous signal emission also provides valuable information related to the flow and velocity of these actively moving object 100 signal emitters 101.

In one embodiment, the location of each circulating object 100 signal emitter 101 can be calculated in (near) real-time or can be determined and analyzed by the program recording the raw signal information in list mode and then the program performing the analysis in a delayed, non-real time fashion. This would be important in cases in which the processing could not take place in real-time as signal information is received but rather the signal information would be acquired and then intermittently processed by the processors 108, 103 in a non-real time manner.

In one embodiment, this localizing ability of the program provides important information on internal flow and diffusion characteristics (or lack thereof), which could be of importance for characterizing areas of pathology and optimizing intervention. As an example, when an object 100 signal emitter 101 enters a region of pathology (e.g., liver malignancy), the characteristics of internal blood flow within this tumor may be determined by tracking the location of the object 100 signal emitter 101 as it enters blood vessels supplying the tumor.

Further, in many instances, new and abnormal blood supply pathways are created within malignant tumors (i.e., angiogenesis), which may not be displayed with conventional anatomic imaging techniques, but which are achievable with the present invention. In one embodiment, other flow pathways and characteristics such as velocity, turbulence, and directionality, can be determined by the program, which would not be expected with most conventional imaging technologies other than ultrasound.

In one embodiment, the program of the present invention provides a detailed 4-D anatomic map of the tumor, its internal characteristics, and its blood supply (i.e., both inflow and outflow) for the user on the display 105. The resulting anatomic map and flow characteristics can subsequently be used by the user and/or the program to optimize treatment strategies (e.g., local delivery of chemotherapy, thermal ablation, external or internal radiation, or cryotherapy). In addition, repeated anatomic and flow mapping by the program pre- and post-therapy, provides for the user an in-depth assessment of treatment response in a variety of measures including (but not limited to) change in tumor volume, internal consistency, blood flow, and metabolism.

In one embodiment, the present invention also offers the option of using different types of object 100 signal emitters 101 and/or receivers 106/107 in order to diversify the data used in analysis and mapping. This use of a variety of different classes of object 100 signal emitters 101 and/or receivers 106/107 can lead to the program creating a hybrid anatomic and functional map by simultaneously acquiring different types of data and multi-channel information from those objects 100. In this specific embodiment, several different types of object 100 signal emitters 101 may be introduced into the host subject and emit their own unique signal as they circulate throughout the organ system of interest. Each individual signal can be analyzed by the program and combined with its partners (i.e., similar signal frequencies) for the program to produce both comprehensive and selective anatomic visualization displays. This could be particularly beneficial when each different class of object 100 signal emitters 101 has its own unique functionality and/or structure.

In one exemplary embodiment, suppose some object 100 signal emitters 101 are of different size or composition, which allows them to circulate in certain anatomic regions not readily accessible by another class of object 100 signal emitters 101. Since each individual class of object 100 signal emitters 101 would have its own unique transmission signal frequency, distribution, and/or pattern of signal, the resulting anatomic maps created by the program could be in accordance with data obtained from each individual class of object 100 signal emitters 101. This would ultimately lead to the program creating a complex multi-channel functional and anatomic map which could be especially useful when diagnosing and/or treating complex disease processes.

In one embodiment, certain object 100 signal emitters 101 may have a unique structure or composition, which allows them to be selectively attracted to certain types of anatomy or pathology. In this example, the electrochemical, charge, or morphological characteristics of a specific class of object 100 signal emitters 101 may cause it to become attracted to specific areas of pathology (e.g., infection). As these object 100 signal emitters 101 coalesce at the infection site, their selective signal frequency can provide an in-depth anatomic map of the focal area of pathology, which can be visually differentiated by the program from other classes of object 100 signal emitters 101.

In one embodiment, where the object 100 signal receivers 106/107 are positioned outside of the host subject (see for example, pancreatic control device 304 in FIG. 3C), the receiving technology can be placed over a narrowly focused region of anatomic interest (e.g., orbits), a broader region of interest (e.g., abdomen), or the entire body. The program-derived visualization maps can in turn be focused, regional, or comprehensive. The processing by the program of these received signals and conversion to a visual image display on display 105 would be based upon the location, magnitude, and directionality of the transmitted signals from the objects 100.

In one embodiment, while the program of the present invention is capable of producing the anatomic visualization map from data from the objects 100, the program can also utilize other data sources in combination to produce a hybrid visual display. Existing examples of hybrid imaging sources include MRI spectroscopy, positron emission and computed tomography (PET-CT) and multispectral optoacoustic tomography. The combined anatomic display produced by the program with alternative imaging technologies such as these, could result in complementary physiologic and anatomic information which can be synergistic in diagnostic and treatment applications.

In one exemplary embodiment, a 4-D visualization map of the heart created by the program of the present invention can be combined with a conventional cardiac nuclear medicine scan. The program's 4-D anatomic display of the heart and coronary arteries would provide high resolution imagery of cardiac and vascular anatomy, along with functional and physiologic data to the user. In this example of cardiac mapping, the functional data which can be derived from the program may include (but not limited to) flow disturbances in the coronary arteries, abnormal function and contractility of myocardium (i.e., heart muscle), disturbances in cardiac rate and rhythm, and abnormal flow and function of the cardiac valves during the various phases of the cardiac cycle.

In this exemplary embodiment, the cardiac nuclear medicine scan could provide functional information on cardiac perfusion during rest and active exercise, but without the high-resolution detail and dynamic data available on the 4-D visualization map. When combined by the program, these two separate imaging datasets could provide synergistic data relating to anatomy, temporal change, physiology, and pathology.

Further, regarding this exemplary embodiment—suppose the 4-D anatomic display shows a 70% stenosis of the right coronary artery with minimal collateral formation. Based upon this anatomic change, one might assume that the diseased right coronary artery requires therapeutic intervention. However, when this information/data is combined by the program with the myocardial perfusion data obtained from the nuclear medicine data, the program will show the analysis on the resulting display (i.e., display 105) that the area of myocardium supplied by the right coronary artery is perfusing normally, meaning that the anatomic occlusion may not require intervention, due to the presence of non-visualized collateral flow. While the 4-D visualization map of the present invention demonstrates the presence and anatomy of these collateral vessels, their relative contribution to myocardial perfusion would not be as readily determined by the program without the additional data supplied by the cardiac nuclear medicine scan. The 4-D visualization map of the present invention would, however, allow anatomic and functional analysis pre- and post-intervention (e.g., exercise, medication).

In one embodiment, the ability of the program to conduct analysis of anatomic and physiologic data over a prolonged time period, also provides the ability to assess in vivo response to different forms of therapeutic intervention for the user. In the example of a 70% right coronary artery stenosis associated with ischemia, a trial of medical therapy may be contemplated by the user using a beta-blocker. Based on the ability of the program of the present invention to perform dynamic visual and functional mapping over time, one can directly compare visualization maps before and after medication to assess its clinical efficacy. Using the present invention, a variety of medications can be administered over time for program comparative assessment of individual drug efficacy specific to an individual patient and pathology. This unique ability of the present invention is in large part due to the objects' 100 ability to provide continuous and dynamic anatomic and functional data which is not available through conventional medical imaging technologies.

In one embodiment, the present invention can also serve as a real-time visualization tool in the performance of interventional procedures, including (but not limited to) biopsies, drainages, catheter or stent placement, and surgical procedures. In conventional practice, when medical imaging is used in the assistance of these procedures, it is routinely done in a static and intermittent manner, with new imaging required each time an operator inserts or adjusts positioning of a given device or instrument.

In the example of a pulmonologist or radiologist performing a lung biopsy under computed tomography (CT) guidance, each time the biopsy needle is adjusted, a new set of images is required. This results in numerous imaging sequences, excessive radiation exposure, prolongation of the procedure, increased risk of iatrogenic complication (e.g., pneumothorax or collapsed lung), increased patient discomfort/fatigue, and increased motion artifact. An alternative technology for image guidance would be fluoroscopy, but this has limitations of both excessive radiation exposure and reduced anatomic resolution.

With the present invention, these pitfalls are minimized due to the fact that visualization mapping by the program is continuous and dynamic. Each time the needle is adjusted by the user, newly updated anatomic images are available to the user in real-time, or near real-time, by the program. In addition, almost all of the forms of energy which can be used in the present invention are non-radioactive, resulting in no ionizing radiation to the patient or operator.

Thus, the present invention provides a theoretically superior method for image-guided interventional procedures due to the program creation of a 4-D anatomic visualization map which is continuously updated, accounts for physiologic and patient motion, produces high resolution imagery, and may avoid ionizing radiation.

But aside from supporting image-guided interventional techniques performed percutaneously, the present invention also provides a unique and novel method for another type of in vivo intervention, which is not available with current technology, such as the user of smart medical devices which included embedded biosensors and miniaturized devices incorporated within various types of medical devices, as described in the Incorporated patents/patent applications. The creation of such a multi-functional smart medical device provides a number of diagnostic and therapeutic in vivo capabilities.

In one embodiment, a wide array of potential interventional options is made available by the program by the different types of embedded miniaturized devices 100 (see the Incorporated Patents) which can be incorporated into a smart device 100 including but not limited to localized drug delivery, biopsy, microsurgery, thermal ablation, cryotherapy, embolization, and cauterization. But the efficiency of such intervention is predicated by the program based on optimal positioning of the smart medical device 100 relative to the pathology of interest. The more accurate and stable the positioning of such a smart medical device 100, the greater the success of the intervention and the lower the complication rate and associated morbidity.

In conventional practice, assessment of medical device positioning is usually done via radiography immediately following placement, with intermittent follow-up imaging performed on an as-needed basis. Since medical devices are frequently prone to positioning change, this can often go unnoticed. In addition, longstanding placement of medical devices are often prone to various types of iatrogenic complications (e.g., diminished function, bleeding, infection).

In contrast, the present invention provides a novel method for combatting these deficiencies. Complications such as bleeding or infection will produce visible pathologic change in the area surrounding the medical device, which will be visible on 4-D visualization maps created by the program. Equally important is the ability of the program of the present invention to continuously monitor positional change of a given medical device, along with the unique and unprecedented ability to intervene using the smart devices 100 when needed (i.e., perform drug delivery, biopsy, microsurgery, thermal ablation, cryotherapy, embolization, or cauterization etc.).

In addition to evaluating smart devices 100 (see for example, smart device 206 in FIG. 2C) positioning through the intrinsic capabilities of the invention, signal transmitters 214 and/or signal receivers 215 can also be directly embedded within the smart device 206 disposed in the body 211 (e.g., in blood vessel 210 in FIG. 2C), which serves as a more advanced and accurate method for monitoring smart device 206 positioning. In one embodiment, signal transmitters 214 embedded within the smart medical device 206 can transmit signals which can be used to localize the medical device 206 in 3-dimensional space, as well as define the architecture and positioning of sensors/devices 213 which are embedded within the smart device 206. Microscopically small changes in device positioning can be characterized by the program, resulting in a 4-dimensional graphical display of the device 206 and its relationship to neighboring anatomy and pathology.

Since the internal power supply 207 of these embedded objects 206 may be short-lived, an external power supply (i.e., external charging mechanism 207, 112, 212) as noted above, may be required. This can be readily applied whenever external signal activation is required.

In one embodiment, smart medical devices 100 may be temporary or permanent in duration. Examples of temporary smart devices 100 may include (but are not limited to) vascular or bladder catheters, intravascular balloon pumps, drainage tubes, and short-term surgical hardware. Examples of permanent smart devices 100 may include (but are not limited to) vascular stents, pacemakers, infusion pumps, arthroplasties, prosthetic valves, and permanent surgical hardware. Embedded sensors 213 within these devices 206 may be multi-functional in nature, and when serving as signal emitters and/or signal receivers (instead of separate devices), these can provide high resolution anatomic and functional 4-D maps. In addition, their fixed location provides the additional advantage of having a well-defined anatomic reference point and localizer.

In one embodiment, by utilizing different signal frequencies or signature signals between the medical device 206 and other circulating object 100 signal transmitters 101, a clearcut distinction can be made between the different types of object 100 signal transmitters 101. At the same time, each individual signal transmitter 214 within the medical device 206 can operate at its own unique frequency and/or provide its own unique signature to the processor 103, thereby allowing the program to create a detailed graphical display of the entire medical device 206 and its individual components. This becomes important when large medical devices 206 are being evaluated and the exact positioning of its individually embedded sensors 213 and instruments is important for performance at a granular level.

In one exemplary embodiment, if microsurgery is being performed on a 1 mm arterial injury, it is important to align the miniaturized surgical tool (e.g., cutting tool 401, see FIG. 4A) embedded within the smart device 400 walls with the very small focus of arterial injury. This may require positioning of the medical device 400 with a small margin of error such as less than 1 mm, while also taking into account physiologic motion. In one embodiment, if signal transmitters 402 embedded within the smart device 400 are positioned at 5 mm intervals, the resulting visualization map created by the program must be able to demonstrate the anatomic positioning of the device 400 in tow as well as the positioning of each of the device's 400 individual components (e.g., cutting tool 401, needle 407) relative to surrounding anatomy and pathology. By having signal emitters 402 and receivers 403 embedded within the smart device walls 404, high degrees of resolution and anatomic localization can be achieved by the program.

In one exemplary embodiment, take a 2 cm liver tumor of uncertain etiology. At the time of surgical biopsy, smart device 100 signal emitters 101 and/or signal receivers 102 can be placed within metallic clips or sutures (not shown), which have been deposited within and/or about the periphery of the tumor. When these signal emitters 101 are activated, they emit signals using a unique frequency, which allows them to be differentiated from circulating smart device 400 signal emitters 402, for example. At the same time, object 100 signal receivers 106/107 have also been positioned in and about the tumor, which can serve an important function in the event that future intervention is contemplated using a smart medical device 400 containing signal emitters 402. As a result, the peritumoral surgical clips/sutures have the ability to serve as both signal emitters and receivers at fixed anatomic positions.

In this exemplary embodiment, after completion of the liver biopsy, pathology results indicate the tumor in question is a malignant hepatocellular carcinoma. Based upon genomic analysis and staging performed by the program, it is determined by the user and/or the program that the optimal treatment should be local chemotherapy infusion. Since the smart medical device 400 contains the capability for pharmaceutical storage (e.g., reservoir 405) and delivery (i.e., needle 407), it is decided by the user and/or program to deliver the chemotherapy to the tumor site via a smart medical device 400. Embedded within the medical device are a series of signal emitters 402 and receivers 403, which will assist in anatomic localization and navigation to the tumor site.

In this exemplary embodiment, as the smart medical device 400 travels towards the liver, the continuous array of signal transmissions by the signal transmitters 402 and receivers 403 to and from the medical device 400 and liver tumor assist in navigation. The combined object 400 signal emitters 402 and receivers 403 located both within the device 400 and the tumor (not shown) effectively act as beacons, which help ensure that the medical device 400 properly positions itself relative to the tumor. Since the drug reservoir 405 and injection needle 407 of the smart device 400 are located at a specific position within the smart device 400, it is essential that they be positioned in close proximity to the liver tumor margins, so as to maximize drug delivery and minimize the potential for the toxic chemotherapeutic or immunotherapeutic agent to be released into the bloodstream and cause systemic complications.

In this exemplary embodiment, repetitive signals are transmitted between the smart device 400 and the liver tumor, providing continuous feedback for optimal localization by the program and/or user. Once the device 400 has been properly positioned relative to the liver tumor margins by the user and/or program, the device delivery needle 407 which will be used for the infusion of the chemotherapy drug must be optimally aligned with the tumor. As signals are transmitted between the device 400 and the tumor, the device 400 can be carefully navigated to optimize alignment using sensors 406 (e.g., distance sensors 406), which is aided by the program's 4-D visualization map shown to the user.

In this exemplary embodiment, following completion of the focal chemotherapy infusion, response to treatment over time can be performed by measuring the tumor volume using the program's 4-D visualization map. At the same time, distance sensors (not shown) contained within the deposited surgical clips or sutures which have been positioned at the tumor margins provide enhanced detail of tumor morphology, composition, and size.

In one embodiment, another unique feature of the present invention becomes applicable when analyzing pathology in which the object signal emitters 101 and signal transmitters 100 are in close proximity to one another. Since the signals travel short distances in these circumstances, the quality of the signals is enhanced and less prone to distortion. In such a scenario, qualitative analysis of the signals by the program may reveal important diagnostic information which may not be readily available.

To illustrate this feature, in the above exemplary embodiment of the liver tumor which has been treated with focal chemotherapy from a smart medical device 400, tumor cells which have been killed by the chemotherapeutic agent will often undergo necrosis (i.e., liquefaction) upon death and as such, will have an entirely different internal composition than tumor cells which remain intact and are solid. Signals from the objects 100 which pass through two area of tumor—one solid (i.e., residual tumor) and one necrotic (i.e., destroyed tumor)—will have entirely different waveform characteristics and as such can be readily differentiated from one another by the program. An analogous situation can be seen with ultrasound signals, which are excellent at differentiating between different tissue types such as soft tissue, fluid, calcification, and air.

In one embodiment, since the signals from the objects 100 are being continuously transmitted, stored, and analyzed by the program to produce a 4-D visualization map, it is easy to compare the internal characteristics of waveforms as a given anatomic location over time, effectively presenting a before and after comparative analysis. In this example, localized visualization maps and corresponding signal waveform analysis by the program at the tumor site over time will clearly show temporal change in appearance and composition of the tumor which can provide valuable insight to the user related to tumor activity.

In one embodiment, as experience with such qualitative signal waveform analysis expands over time, an entirely new depth in signal waveform analysis can be achieved by the program relating to anatomic/pathologic correlation, specific to a given anatomic location, tissue type, pathology, and clinical context. To illustrate this using another example, suppose a patient has had a tibial fracture treated with surgical fixation (e.g., side plate and screw fixation). In one embodiment, object 100 signal emitters 101 and signal receivers 106/107 embedded within the surgical hardware and adjacent bone at the time of surgery can be used to transmit signals that are evaluated by the program to determine fracture healing over time, and the program can provide a before, during, and after a 4-D visualization map.

In one embodiment, the signals transmitted by the objects 100 disposed about the fracture margins can show the various phases of fracture healing which includes hematoma formation, fibrocartilaginous callus formation, bone callus formation, and bone remodeling. Since a large number of fractures result in delayed and/or failed healing (i.e., up to 10%), it is important to recognize this as soon as possible in order for the program to determine that an intervention is warranted and alert the user. Common causes for failed healing include inflammation, infection, and diminished blood supply. In addition, common risk factors include old age, obesity, diminished bone mineralization, malnutrition, and certain drugs.

The present invention provides the ability to continuously monitor the healing process at the fracture site through localized object 100 signal analysis by the program and identify potential complications at a far earlier time than conventional diagnostic techniques allow. In the event of a post-operative infection preventing bone healing, early diagnosis and intervention can dramatically improve clinical outcome and reduce associated morbidity and the potential for reoperation. This is just one of many practical examples where qualitative signal analysis performed by the program can provide new innovation opportunities in early diagnosis and treatment, specific to the clinical context.

In one embodiment, the present invention utilizing embedded object signal emitters 101 and/or signal receivers 106/107 within objects 100 (or smart devices such as smart devices 206, 400) is particularly applicable in the setting of surgery. Since surgery involves the implantation of a variety of manmade objects (e.g., hardware, sutures, clips, drains), there is a unique opportunity for the program of the present invention to continuously record in memory/data storage 118 and analyze post-operative change in both healing and iatrogenic complications.

Since a wide array of energy sources (e.g., internal energy sources 111, 207, 416 (see FIG. 4B), external energy sources 112, 202, 209, 212) can be utilized in the invention, in one embodiment, the decision as to what type of object 100 signal emitters 101 and receivers 106/107 to select may be tailored to the specific task at hand. In one exemplary embodiment, suppose a patient has undergone appendectomy after a ruptured appendix. In this clinical setting, a common post-operative complication is the development of post-operative fluid collections at or near the operative site. These fluid collections can include (but are not limited to) seroma, hematoma, and abscess. The post-operative clinical course of the patient and treatment requirements greatly vary in accordance with the specific type of post-operative complication encountered. In the event that an abscess was to develop (which is quite common following appendiceal rupture), it is essential that the diagnosis and intervention occur quickly, or else the patient could become extremely ill (i.e., septic) and even die. In current practice, diagnosis is often delayed and dependent upon medical imaging technologies which require substantive change over time, before the diagnosis becomes evident.

In this exemplary embodiment, in order to proactively assess post-operative healing and potential complications in such a high-risk patient, one can embed object 100 signal emitters 101 and/or receivers 106/107 about the operative site, utilizing the surgical hardware and/or drains which are routinely placed. This will allow the program to perform the following to yield clinical advantages:

1. Actively evaluate post-operative healing.
2. Early detection of post-operative complications.
3. Ability to assess anatomic and pathologic change over time, on both microscopic and macroscopic levels.
4. Analyze pathology in accordance with the unique signal characteristics of the signal transmissions.
5. Serve as anatomic guides for intervention (which is of particular benefit in the navigation of smart medical devices (e.g., smart devices 206, 400)).

In one embodiment, the specific selection of objects 100 is another important feature of the invention and this application. In one exemplary embodiment, if a common post-operative finding in a post-appendectomy patient is fluid accumulation, then an object 100 which has sensors 113 which are both sensitive and specific to fluid such as ultrasound, may be an ideal choice. At the same time, if and when such a fluid collection is detected by the program analysis of the signals, the next question is what specific type of fluid collection is involved. Since percutaneous aspiration is invasive and involves morbidity and potential complications, non-invasive diagnosis is preferable. In addition, the fluid collection would have to reach a critical size before aspiration is technically possible. All in all, it is far more preferable to utilize the present invention to detect the complication non-invasively and early on in its development, when the fluid collection is small.

While ultrasound is an ideal candidate for detection of post-operative fluid, it is relatively nonspecific in identifying the internal contents of fluid collection. Since infection is the complication of greatest clinical significance, in one embodiment, a secondary object energy type (i.e., for a type of object 100) may be required, which is synergistic to the information provided by ultrasound. In this scenario of potential infection, in one embodiment, the two candidates may be object 100 signal emitters 101 utilizing thermal energy (since infection is associated with increased inflammatory response and heat), and white blood cell (WBC) tagged signal emitters 101.

In one embodiment, when the program combines the program-created ultrasound visualization map with the program-created thermal or white blood cell (WBC) visualization maps (i.e., dual visualization maps), improved detection of anatomy and pathology is provided to the user and is more accurate than a single visualization map. This example shows how selection of the specific type of object 100 signal emitter 100 and the combination of multiple objects 100 signal emitters 100 may be beneficial to early and more accurate diagnosis, and how internal signal analysis by the program is important in pathologic diagnosis.

In the prior exemplary embodiment, when an ultrasound signal is used, the resulting waveforms are particularly good at differentiating air, solid, tissue, and fluid due to the internal characteristics of the ultrasound waveforms. However, one issue that requires attention lies with the relative lack of specificity when differentiating complex fluid collections from one another (e.g., liquefied hematoma versus abscess). However, with the present invention, the WBC visualization map can be combined with the ultrasound visualization map to resolve this issue. Thus, limitations in pathologic specificity inherent to a single visualization map can be addressed through the combination of a second visualization technique which is combined by the program to form the dual visualization map. This combination of ultrasound and WBC imaging by the program is important in the differentiation of a complex cystic collection which would include abscess as one of the possible etiologies.

In another embodiment, the present invention can be applied to long term patient care where the program has the ability to selectively activate the internally embedded objects 100 in an automatic or manual fashion, at either predetermined or newly desired time intervals. In one exemplary embodiment, a patient has had implantation of a permanent medical device (e.g., heart valve or orthopedic prosthesis 305 (see FIG. 3A)). As part of the patient's routine preventative care, the physician of record may request the program to provide an automated visual map of the respective device 305 and surrounding anatomy on a bimonthly basis. The embedded objects 305 signal emitters 306 and/or signal receivers 307 in these devices 305 would become automatically activated at the designated time periods and the program would create the corresponding visualization map and signal analysis.

In this exemplary embodiment, since the patient's baseline postoperative data is readily available for comparative analysis by the program, the newly acquired data are compared by the program with the baseline data and/or associated follow-up maps and analyses by the program. The new and prior data can be manually reviewed, or preferably automatically interpreted by the program using computerized artificial intelligence (AI) techniques (e.g., computer-aided diagnosis). In addition, these analyses by the program can be enhanced by the program applying temporal subtraction to the corresponding datasets (i.e., visualization map and signal analysis) to highlight any interval changes which may have occurred. The resulting findings by the program are saved in the database 118 and are conveyed to the ordering physician by electronic methods (i.e., e-mail, fax, etc., as with all alerts), with subsequent action taken by the physician if required.

In one embodiment, the program allows for manual activation in addition to predetermined automated signal activation and analysis, in the event that a clinical concern was to arise. In one exemplary embodiment, the patient is experiencing symptoms referable to the device 100 or the structural integrity of the device 100 is of concern based upon signals received by the processor 103 (i.e., visualization map by the program shows an issue, or device 100 signals are dropping, attenuated, above a predetermined threshold, an energy source issue etc. (see below for further descriptions)), the physician may elect to manually activate the object 100 embedded signal emitters 101 and/or receivers 106/107 for an unscheduled analysis by the program. The same process of automated interpretation by the program (or manual interpretation) can subsequently be performed. In one embodiment, as indicated in the Incorporated Patents, the object 100 can also be instructed to be removed from the body as waste, be moved to a particular location in the body for future collection, be turned off, or collected by another smart device 100 to be removed from the body, etc.

In one embodiment, the ability of the program to activate embedded object 100 signal emitters 101 and/or receivers 106/107 at desired time periods is another unique feature of the present invention. In addition to external human activation, the embedded object 100 signal emitters 101 and/or signal receivers 106/107 may also be activated through predefined clinical algorithms. In one exemplary embodiment, suppose a patient with a cardiac pacemaker has an episode of rapid heartbeat (i.e., tachycardia). Under normal conditions, the pacemaker would have become automatically activated, but, in this particular circumstance, it did not. The failure to automatically activate the pacemaker, and tachycardia detected by the program, may serve as an automatic trigger for the program to instruct the embedded object 100 signal emitters 101 and/or signal receivers 106/107 to create a visualization map to assess pacemaker integrity and positioning.

In one exemplary embodiment, the feature of dynamic automated signal activation by the program can take place, using the example of an elderly patient who has undergone a hip replacement (i.e., arthroplasty) as a result of a prior hip fracture. The orthopedic surgeon has utilized the program of the present invention to create an automated visualization map and signal analysis to take place every three (3) months which is interpreted via AI, with the results automatically forwarded to him by the program by electronic methods (i.e., email, fax etc.).

In this exemplary embodiment, in addition to these automated signal activations every three months, a number of additional clinical parameters can be established by the user which will produce an automated trigger for signal activation. For example, one of these automated triggers is any detected device movement from its predetermined position, greater than a predetermined amount (i.e., 1 mm) on sequential visualization maps. Further, the user may trigger the program when the patient reports increasing and/or unexplained pain in the postoperative hip. Thus, activation of the objects 100 by the program can take place by automated trigger or through patient input.

In this exemplary embodiment, where abnormal prosthesis movement is of concern, the program will create continuous visualization maps to take place over a 24-hour period. This will provide the user with a display of a dynamic visualization map of the prosthesis and surrounding anatomy over a prolonged time period, so that the user can identify any subtle change which may not be evident with a single isolated visualization map. As the continuous data is collected and analyzed by the program, small (e.g., 2 mm) increments in device positional change can be identified in this example, about the femoral diaphyseal component of the prosthesis, indicative of early prosthesis loosening, which would not be evident through conventional diagnostic techniques. One of the causes of prosthesis loosening is infection, which in its early stages may often go unnoticed. Early diagnosis and treatment is essential in order to avoid the need for prosthesis removal and repeat surgery.

Thus, in this exemplary embodiment, along with the program's creation of dynamic longitudinal visualization maps, the qualitative analysis of the signals by the program may also serve as a valuable diagnostic tool in this exemplary patient. In addition to the creation of the visualization maps by the program, which demonstrate the subtle device movement (which may be determined to be dynamically exacerbated with certain types of movement), the corresponding signal analysis by the program may demonstrate early infection at the device-bone interface. Once diagnosed by the clinician, the patient is started on antibiotic therapy and continuous signal analysis and visualization mapping is performed by the program over the next two weeks to ensure therapeutic response.

In one embodiment, as these signal waveform analyses by the program are conducted over time and involving large numbers of hosts, one can effectively create an artificial intelligence (AI) program for automated signal analysis. This would effectively create the ability to automate waveform analysis using the program and avoid the potential pitfalls of inter and intra-observer variability in the interpretation process.

In one embodiment, since medical devices (i.e., hip replacements, pacemakers, heart valves or prostheses, etc.) are prone to mechanical breakdown and performance failure, another important application of the present invention is the structural and functional assessment of medical device integrity and operational performance. In addition to using the object 400 signal emitters 402 and/or signal receivers 403 to create visualization maps, the signals can also be used by the program to map the architecture and topography of the medical devices (not shown), localize internal components (including sensors and miniaturized devices—not shown), and analyze for physical defects. This would be analogous to the use of ultrasound in the detection of structural defects as small as 1-2 mm in aircraft through the analysis of carbon fiber reinforced polymers (CFRP).

In one embodiment, a wide array of structural defects can occur in medical devices (i.e., hip replacements, heart valves or prostheses, etc.) which can adversely affect performance as well as cause risk of iatrogenic complications to the patient. Rather than wait until such a defect become clinically evident, at which time the clinical manifestations are serious, and the intervention options limited, the program of the present invention can proactively analyze both the internal components of a given medical device, as well as its overall structure and performance, using the objects 100 of the present invention.

In one exemplary embodiment, a microleak has occurred at the periphery of a heart valve 305 which has embedded sensors 308 and signal emitters 306 and receivers 307. During the course of a routine quality control analysis by the program, the visualization map created by the program of the valve 305 and surrounding anatomy could show changes that would detect this leak. In addition, the combined 4-D anatomic and functional assessment by the program of the valve 305 and surrounding anatomy, could visualize the leak, any potential damage to the surrounding tissue, expansion of the leak during different phases of the cardiac cycle, characterize the internal characteristics of any resulting fluid collection, and (perhaps most importantly) the change in the leak over time. In one embodiment, based on the program's analysis of the structural defect in the device 305 and its performance, an intervention plan can be developed before the patient was to incur a serious complication. One option could potentially consist of microsurgery, performed by a smart device 400.

In another exemplary embodiment, is the unique ability of the program to create automated notifications in the event that device 100 positional change exceeds a predetermined threshold. This threshold can be established by the user, or recommended by the program using AI, in accordance with the individual patient, clinical context, anatomic location, and type of device. In one embodiment, in the event that a device positional change was to take place that exceeded this threshold, an automated alert via electronic methods (i.e., email, fax etc.) could be transmitted by the program to the designated healthcare provider to determine next step requirements.

In this exemplary embodiment, such a clinically important device positional change can be illustrated with an endotracheal tube. In most circumstances the endotracheal device (not shown) is inserted to terminate a few centimeters above the trachea. However, it is fairly common for endotracheal tubes to change positioning, often by several centimeters. If the distal end of the tube was to become advanced into one of the mainstem bronchi, then only one lung would be mechanically aerated and the other lung would incur atelectasis (i.e., collapse) due to absence of mechanical airflow. Simple patient movements such as neck flexion can result in this type of tube migration, which will often go undetected for hours or even days.

In this exemplary embodiment, at the time of endotracheal device (tube) placement, the responsible physician could input positional parameters for the endotracheal device, including the outermost acceptable positional coordinates. If and when these positional parameters were to become violated as determined by the program during its monitoring and analysis, an automated alert would be sent by the program via electronic methods, notifying the physician, who in turn could determine what course of action was required. In a situation such as this, the intervention would often be as simple as a minor change in tube positioning.

In one embodiment, positional changes of objects 100 or smart devices 100, 206, 400 of the present invention may often be performed in vivo and with minimal active intervention. This is because the objects 100 or smart devices 100, 206, 400 of the present invention have the ability to possess internal navigation capabilities (i.e., propulsion device 110), which when combined with the invention's 4-D anatomic localization abilities (i.e., distance sensors 113) can result in automated medical device positional correction capabilities. As stated in the Applicant's incorporated patent applications, smart devices 100, 206, 400 may possess self-propulsion capabilities, which allow the devices 100, 206, 400 to travel independently within an aqueous, gelatinous, or air-filled environment.

In one embodiment, there are two distinct options for smart device navigation: 1) self-directed, or 2) externally directed navigation. In one embodiment, the embedded signal emitters 101 within the smart device 100 transmit a continuous signal, akin to a beacon, and receivers 106/017 on the smart device 100 receive signals transmitted to the object 100 from external sources (i.e., wireless transmitter/receiver 102 etc.). In external navigation, an authorized operator, after the smart device 100 has been inserted and turned on (see step 500, FIG. 5) can navigate the medical device 100 to a desired anatomic location (e.g., tumor site) (step 501, FIG. 5), by issuing directional commands via wireless transmission to the object 100 processor 108 (step 504, FIG. 2), which in turn instructs the propulsion system (e.g., arms 110 or whip-like tails 122) via propulsion mechanism 119 to move in a particular direction. Thus, the operator can transmit signals to the smart device 100 navigational control module of the processor 108 instructing directional movement (analogous to a video game controller).

In one embodiment, in the alternative strategy of self-navigation, the smart device 100 navigates on its own, based upon continuous feedback of signals being transmitted from object 100 signal emitters 101 and/or receivers 107 contained within the device 100 (which determines its position and directional movement), and corresponding object 100 signal emitters 101 and/or receivers 107 contained within the target location (e.g., liver tumor) and/or nearby circulating object 100 signal emitters 101 and/or receivers 107. In one embodiment, the continuous transmission of these guidance signals provides a method in which the smart device 100 can self-navigate to a desired anatomic location of interest. When both the smart device 100 and target site have embedded object 100 signal emitters 101 and/or receivers 106/107, the bidirectional communication between these two locations creates the ability of a self-directed internal navigation system with continuous feedback to and from the object/device signal emitters 101 and signal receivers 107.

Figure 5:
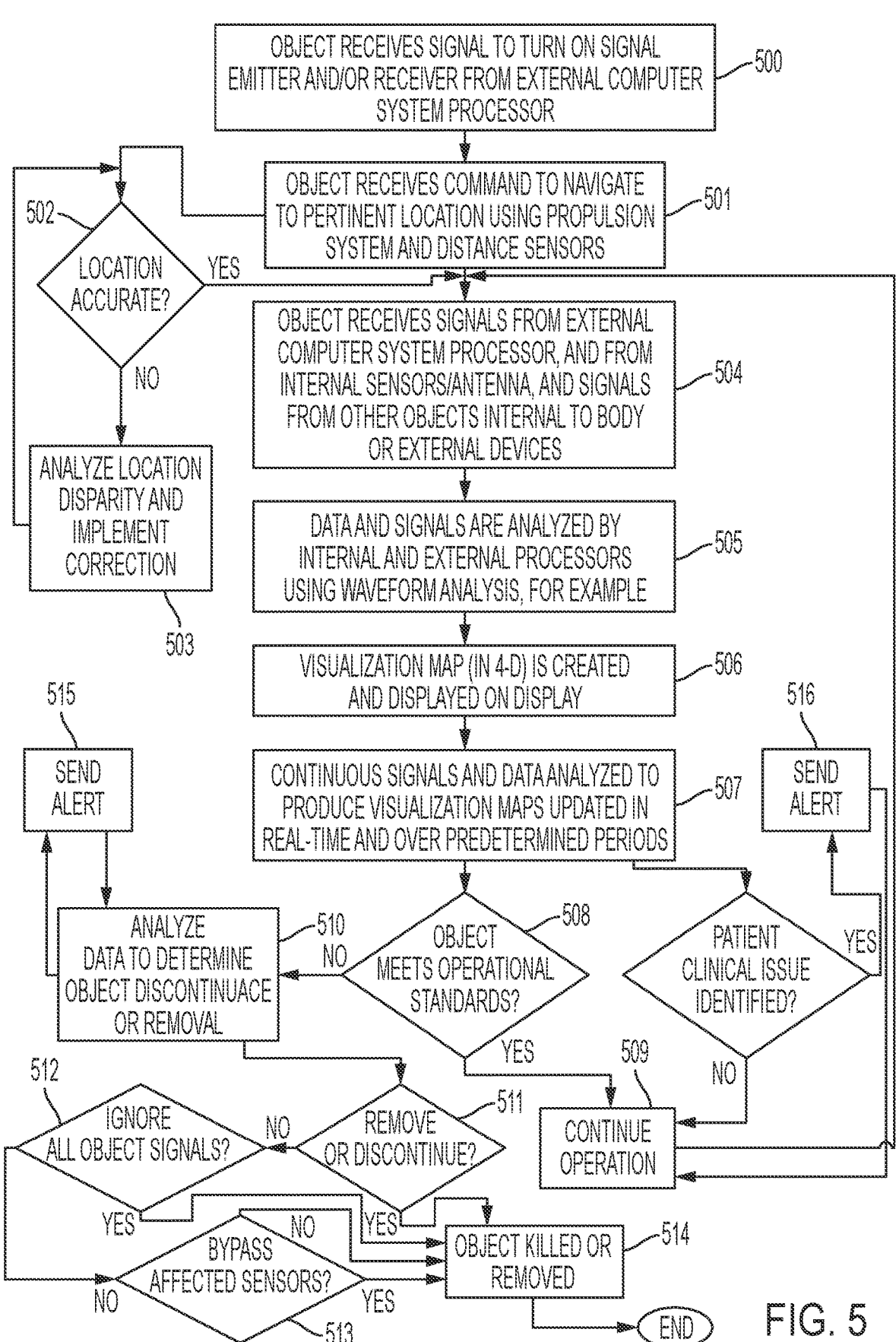
FIG. 5 is a flowchart which shows the basic algorithm of the operation of the object signal emitters and/or receivers or smart devices of the present invention as a series of steps, according to one embodiment consistent with the present invention.

In one embodiment, as discussed above, if the location of the object 100 is not accurate, or it has moved over time (step 502, FIG. 5), the program can analyze the signals from the object 100 and surrounding objects 100 to determine the location disparity and implement a correction (step 503, FIG. 5).

In one embodiment, where the target location does not have embedded object 100 signal emitters 101 and/or receivers 107, an alternative strategy would be for the program to utilize the data and signals from the object 100 (step 505, FIG. 5) to create the 4-D anatomic visualization map (step 506, FIG. 5) and to define 3-dimensional coordinates of the target site, which can be inputted into the smart device 100 as a navigational command. As circulating microbots 100 and/or nanobots 100 travel through the host body, the signals they emit and/or receive provide continuous feedback to the smart device 206/400 as to both its anatomic location as well as the desired target site location, in addition to the clinical information in real-time (step 507, FIG. 5).

In the exemplary embodiment of the liver tumor where the desired function is local infusion of chemotherapy contained within a drug reservoir 405 embedded in the medical device 400 (see FIG. 4A); by knowing the architecture of the medical device 400 and location of its embedded technology, one can determine that the reservoir 405 is located 4 mm anterior to the nearest signal receiver at the tumor location (not shown). Using the program to correlate the device 400 signal receiver 403 location with the tumor location (based on transmitted signals from the tumor location and the program's 4-D anatomic visualization map), the operator can externally direct positioning of the medical device 400 using directions to propulsion device 408 (e.g., chemically powered motor), so that the injection needle 407 and drug reservoir 405 are properly aligned with the epicenter of the liver tumor. Once the localization has been verified by program using the updated anatomic visualization map (step 502, FIG. 5), the operator can provide the command to the device 400 having the injection needle 407, for the injection of chemotherapy drugs from reservoir 405 to commence. As the procedure progresses, the continuous signal transmission and analysis provides updates which are analyzed by the program and displayed in the 4-D visualization map, including the spatial relationship between the smart device drug release components and the tumor. Minor adjustments in smart device positioning can be instructed by the program to navigational controls of the smart device 400 and propulsion device 408, to ensure that alignment is optimized and the drug reaches its intended location (steps 502-503, FIG. 5).

In one embodiment, an important component of any technology-driven invention is the ability to proactively analyze quality and identify any performance deficiency before it adversely affects outcomes. In the present invention, quality control of the object 100 signal emitters 101 and/or signal receivers 106/107 can be readily established by the program continuously assessing the large volume of signal data which is being transmitted and analyzed. Since thousands, millions, or even billions of data points are being continuously received and the object 100 signal emitters 101 and receivers 106/107 are in close and well-defined proximity to one another, this provides ample opportunity for the program to statistically evaluate neighboring signals for accuracy and reliability. Since the location of each signal emission and receipt can easily be established by the program analysis, any potential point of failure can be accurately localized by the program as well.

In one embodiment, once an individual object 100 signal emitter 101 and/or receiver 106/107 has been identified as a potential quality concern or not meeting predetermined standards of performance (step 508, FIG. 5), more intensive signal analysis can be performed by the program to determine the accuracy and severity of the performance issue (step 510, FIG. 5). In the event that a given object 100 signal emitter 101 and/or receiver 106/107 has been determined to be faulty (an automated alert can be sent to the user in step 515, FIG. 5), it can be removed from operation or simply turned off through deactivation by the user (step 511, FIG. 5), or automatically upon attaining a predetermined threshold or criteria. The extremely large quantity of data being continuously received and analyzed by the program provides for large sample-size statistics, which heightens the accuracy of the analysis, providing for rapid identification of any data outliers and the decommissioning of the associated objects 100.

In one embodiment, based on the unique signal frequency determined by the program, the aberrant signals and their originator objects 100 can be promptly identified and shut down in a variety of ways. From a passive perspective, their corresponding signals can simply be ignored by the program (step 512, FIG. 5), negating any ill effects of the erroneous data, or if possible, the program may be able to ignore or bypass certain signals which do not affect the desired operation of the object 100 (step 513, FIG. 5). In one embodiment, from an active perspective, the associated microbots or nanobots 100 can be neutralized by the program activating an internal kill switch (destructed or deactivated) (step 514, FIG. 5) which can be externally transmitted to the objects 100 through protected wireless transmission by wireless transmitter 102. The net effect is to continuously ensure that all signals contributing to the real-time data analysis by the program are in alignment to neighboring signals and the resulting data analyzed by the program is reproducible and accurate.

In one embodiment, another unique and important feature of the present invention is the ability to perform anatomic and functional analysis in a portable fashion. In a manner analogous to a Holter monitor, one can have wearable sensors 213 (see FIG. 2B, for an exemplary embodiment) positioned on the patient with the combined capabilities of transmitting and/or receiving signals. These external sensors 213 can in turn communicate with circulating microbots or nanobots 100 internal to the human body, which are used by the program to produce anatomic visualization maps. This portability feature provides the capabilities of creating visualization maps in a variety of urgent care or emergent situations including (but not limited to) at home (in high-risk patients), military operations, critical care environments, airplane or space travel, or assisted living residences. An example of a portable application of the invention is provided below.

To illustrate how the present invention works we will take two examples if its application in real-world scenarios. These will include: 1) an acutely ill patient brought into an emergency room with symptoms of an acute neurological stroke, and 2) a soldier critically wounded on the battlefield. A. Acute Stroke in Emergency Room Patient.

In this exemplary embodiment, an elderly patient with no available previous medical records is brought to a hospital emergency room after being found unconscious. During the triage process, an intravenous injection is given containing thousands of nanobots 410 composed of both signal emitters 411 and receivers 412, whose signals from the signal emitters 411 will be used by the program to generate a whole-body visualization map on display 105.

In this exemplary embodiment, preliminary review of the whole-body images created by the program's visualization map, demonstrates an acute stroke within the left cerebral hemisphere, which corresponds to deficits found on the bedside neurological exam. In the absence of other significant pathology, dedicated brain imaging is performed with application of a cap (not shown) over the patient's head containing embedded signal receivers (see FIG. 2B for an example of external wear with embedded signal receivers 213).

In this exemplary embodiment, with the application of the localized cap containing larger and higher functional signal receivers, detailed visualization maps of the brain are created by the program, which provide high resolution images of the acute brain infarct which is localized in the right cerebral hemisphere in a region supplied by the right middle cerebral artery (MCA).

In this exemplary embodiment, using the velocity measurements from data forwarded to the processor 103 by the objects 410 signal emitters 411, and calculating the travel velocity in the circulating signal emitters 411 from the data, differential flow rates are determined by the program for the major intracerebral arteries, with a small reduction in flow velocity in the affected proximal right MCA, relative to the left MCA. In addition, a focal occlusion is demonstrated from the data by the program, as shown in the visualization map, in a small distal MCA branch, in which no flow is demonstrated.

In this exemplary embodiment, while the visualization maps created by the program show the infarct in question, questions remain for the user as to whether the infarct visualized represents the entirety of damaged tissue, whether the infarcted tissue has the potential to expand and worsen, and what kind of therapy would be most beneficial. In order to answer these questions, additional data is required by the user, that explores the functionality of brain tissue, as opposed to the anatomy alone (which the program's visualization maps have defined).

In this exemplary embodiment, prior to determining the best course of treatment, a functional map created by the program is required, which can more accurately define at risk brain tissue by analyzing brain metabolic activity. In order to provide this functional brain mapping, a second injection into the patient is performed, injecting nanobot 410 signal emitters 411 which have been tagged with glucose (i.e., sensors 413). The purpose of this tagging process is to visualize which areas of the brain are metabolically active and glucose avid, which portions of the brain have reduced metabolic activity (i.e., at risk brain), and which portions of the brain have no metabolic activity (i.e., irreversible cell death).

In one embodiment, the two resulting, different visualization maps (anatomic and functional) created by the program, can be analyzed the program a number of different ways. By the program superimposing the respective areas of brain infarction on the visualization map, it can be displayed to the user that a large area of surrounding brain which is not anatomically abnormal is indeed shown to have reduced metabolic activity on the functional map and thus represents at risk brain tissue, which could be subject to infarction and neuronal death if left untreated.

In addition, in the exemplary embodiment, dynamic visualization maps created by the program over a 45-minute duration show that the infarct has increased in extent by 15%, meaning that the infarct is actively expanding. Based upon the large area of at-risk brain tissue and interval progression, it is determined by the user that urgent thrombolytic therapy is required in the form of tissue plasminogen activator (tPA).

In the exemplary embodiment, once the tPA has been administered to the patient, continued anatomic and functional maps are created by the program, which when analyzed by the program with the baseline visualization maps, shows both the areas of brain infraction and at-risk brain have decreased in size. This shows the results of successful treatment of the acute stroke, which will be continuously monitored by the program over the next 24 hours to ensure no further brain damage occurs.

In one embodiment, one of the major complications of thrombolytic therapy is bleeding, so continued whole-body monitoring by the program is required to ensure patient safety. In one embodiment, in addition to dedicated brain visualization mapping, whole body visualization maps are continuously created and monitored by the program for evidence of bleeding. During follow-up imaging (i.e., visualization map) performed by the program three (3) hours after tPA administration, a new abnormality is identified in the stomach by the user and/or analyzed and identified by the program, which is suspicious for a new area of active bleeding.

In one embodiment, in order to investigate further, a blanket 200 (see FIG. 2B) with embedded signal emitters 220 and/or receivers 203 is positioned over the patient's abdomen and a new injection of object 400 signal emitters 411 (and/or receivers 412) tagged with sensors 413 for red blood cells (RBCs), is administered to the patient. The tagging of the objects 410 to RBCs provides a more detailed assessment of active bleeding. Follow-up visualizing mapping by the program reveals a small 1 cm actively bleeding gastric ulcer. Since the patient remains unstable, endoscopy is not a viable option and an alternative therapeutic strategy is chosen by the physician, using a smart device (not shown) in the form of a nasogastric tube to cauterize the bleeding site.

In the exemplary embodiment, the specific location of bleeding is identified by the user and/or program on the visualization map, and as the feeding tube is inserted by nursing staff, its location is tracked by the program in real-time based on both circulating smart device 410 signal emitters 411 and/or receivers 412 as well as signal emitters and/or receivers embedded in the feeding tube (not shown) walls.

In this exemplary embodiment, it is noted that the nanobots 410 can identify active bleeding on their own due to the fact that they will circulate throughout the blood vessels and just like red blood cells, will become trapped within a site of active bleeding (i.e., hemorrhage), as they pass through the site of injury.

Once they become trapped outside of the blood vessels and within the hemorrhage, their location and associated pathology will become evident on the nanobot-derived 4-D visualization map created by the program. In addition, nanobots 410 also provide information about the size of the hemorrhage and the rate at which active bleeding is taking place, by the data from their sensors 413.

In this exemplary embodiment, when active bleeding takes place in the human body, it activates the coagulation pathway, which is a natural response to counteract and minimize bleeding. During activation of this pathway, a number of substances are produced by the body (e.g., fibrinogen, thromboplastin, and D-dimer). These are essentially biomarkers for bleeding, which could be monitored through biosensors 413 contained within circulating nanobots 410 (which may be nanobots 410 having biosensors 413 specific to red blood cells, which are injected when active bleeding is suspected). In the event that active bleeding was indeed taking place, the nanobots 410 could be detect and quantify the degree of these biomarkers. (Note that the nanobots 410 can contain miniaturized biosensors 413 which provide the ability to perform real-time in vivo biochemical analysis, as disclosed in the Incorporated Patents.)

In this exemplary embodiment, other biomarkers may also assist in localization of the bleeding site as well, since damaged tissue will secrete biomarkers as well. Essentially all organs within the human body have their own unique biomarkers, all of which could be actively monitored by biosensors 413 contained within the circulating nanobots 410. As an example, if the liver is the site of active bleeding, biomarkers specific to liver injury will be produced (e.g., mitochondrial DNA, micro RNA-122, acetylated HMGB-1). Organ and pathology-specific biomarkers provide a unique opportunity for early in vivo diagnosis and localization, through the creation of specialized nanobots 410 with embedded miniaturized biosensors 413.

Once the active bleeding site has been diagnosed, localized, and quantified; therapeutic nanobots 100 can be dispatched to the site of bleeding. These can possess a variety of therapeutic options such as cauterization tools, surgical suturing capabilities, or release of blood clotting agents.

In this exemplary embodiment, after the feeding tube is determined to be within the gastric lumen, as located by the user based on its position in the program-created visualization map, the internal propulsion device (not shown) contained within the feeding tube is activated and the feeding tube slowly advances in 1 mm increments. As the feeding tube advances, its position is continuously monitored by the program in real time. In one embodiment, external navigation of the smart device (not shown) in the feeding tube is activated to advance the feeding tube to the bleeding site. Once proper positioning has been established using the visualization map created by the program, the cauterization tool 424 contained within the smart device 410 is actively aligned with the bleeding site using commands from the user which are translated into instructions by the processor 103 to the smart device propulsion mechanism 426 which activates the propulsion device 425 (i.e., whip-like tails 425).

In this exemplary embodiment, once the exact positioning is confirmed on the display screen 105 by the user, an anchoring device (i.e., hooks, adhesive, pincers 419, clips 420, etc.), either part of the smart device of the tube or a smart device 410 circulating and/or deployed by injection into the patient by the user, is used to prevent the feeding tube from additional movement. In one embodiment, the anchoring device 419, 420 is controlled by the user to navigate to the smart device of the feeding tube, to anchor the feeding tube via physically blocking the feeding tube from moving, or by deploying the anchoring mechanism 419 of the smart device 410 or of the tube's smart device. The deployment of the anchoring mechanism 419 can take form in a variety of ways, including, for example, a spring mechanism 422 which pushes out the pincers 419, or a post 421 that pushes out the clip 420, from recess 427.

In this exemplary embodiment, the cauterization tool 424 (i.e., thermal energy-based), which is either part of the primary device in the tube, or a separate device 410, is then released or deployed from its recess 427 in the smart device 410 by for example, a spring mechanism 423, and is activated by the user. Throughout the course of the procedure, continuous signal transmission occurs from nanobot 410 emitters 411 which is aimed at ensuring the cauterization tool 424 and bleeding site remain properly aligned. In addition, the gastric mucosa is continuously mapped by the program to determine if and when bleeding has terminated. Before the procedure is terminated, a small suture (with embedded signal emitters and receivers) (not shown) is deployed at the bleeding site to serve as a navigational aid if needed in the near future.

In this exemplary embodiment, the devices such as the anchoring tool 420, cauterization tool 424, etc., can be turned on and become active by the program instructing the processor 417 of the nanobot 410, or can be turned off by the processor 417 as instructed by the program when they are no longer needed.

In this exemplary embodiment, since gastric bleeding is often unpredictable, continuous mapping by the program is performed over the next 24 hours. If traditional medical imaging technologies (e.g., CT angiography) were to be used, a number of limitations would exist including (but not limited to) requirement for transport of the unstable patient to the radiology department, contrast injections (which can adversely affect renal and cardiac function), associated ionizing radiation, and requirement for repeated imaging (each of which requires patient transport, contrast administration, and radiation exposure). In addition, these types of imaging studies may be subject to motion artifacts and be operator dependent.

The present invention eliminates most of these concerns due to the program's ability to dynamically and continuously visualize anatomy and/or pathology on the display 105 over a prolonged time period, which is only limited by the lifetime of the nanobot 410 signal emitters 411 and/or receivers 412. Even this limitation can be obviated by the ability to recharge nanobot 410 energy sources 416 through external power sources (e.g., energy sources 221), along with the ability to readminister new smart devices 410.

In one embodiment, as the data is continuously collected and analyzed by the program, a number of different viewing options are possible. One includes creating a cinematic display on the display 105, analogous to a movie, which can selectively target the principal site of pathology. In this case, that represents the distal stomach (i.e., gastric antrum), where the bleeding ulcer is located. The display 105 format chosen includes a continuous display loop of this region, where 1-minute displays are merged together. The purpose of such a display option is to highlight subtle changes in pathology which occur over a defined time period, which may not be evident on static images alone.

In one embodiment, with the emergence of artificial intelligence (AI), the anatomic/pathologic region of interest can be analyzed through computer program software (e.g., computer-aided diagnosis) to identify any change over time, which in turn can trigger an automated alert (via electronic methods) (step 516, FIG. 5) to the operator for further investigation. This reduces the potential for human fatigue and/or error when dealing with large and expansive datasets. In addition, subtle and early changes are more likely to be detected through computerized analysis, since human analysis is often prone to both inter and intra-observer variability.

Another important advantage of the present invention's ability to provide comprehensive imaging data over prolonged time periods is the identification and elimination of artifacts and noise in the interpretation process by the program, along with addressing challenges in fusing disparate datasets in conventional imaging. Since the program of the present invention creates a continuous and dynamic data stream, noise and artifacts which are transient, can be readily identified and eliminated from analysis. As extremely large volumes of data are recorded and analyzed by the program, a single frame of data which has been distorted by noise or artifacts can be readily differentiated by the program from the thousands of data frames which come before or afterwards. Unlike conventional imaging datasets which are static in nature, the dynamic and continuous collection of data by the program provides a reliable method for identifying and removing artifacts which can result in interpretive error.

Turning back to the above exemplary embodiment of a gastric bleed, as the longitudinal data is recorded, cleansed, and analyzed by the program in this particular patient, a dynamic cinematic focus over the gastric antrum reveals no active bleeding over the next 24 hours. The smart feeding tube is subsequently removed by the user and the patient is transferred for routine care.

B. Critically Wounded Soldier on Battlefield

In one embodiment, the methods for signal receiving from the objects 100 and conversion of these signals into an anatomic map (as described above), make it entirely possible to perform the program data analysis and processing on a portable basis, which makes the present invention applicable in a variety of emergent and non-emergent medical settings. An example of such a portable application is provided below in an exemplary embodiment.

In the previous example, the patient was in the controlled environment of the emergency room, which allows direct access to a wide array of technology, data, and medical personnel. But the present invention can also be applied in unstable and unpredictable environments where these supporting measures are not readily available. In one embodiment, this can be accomplished by the adaption of wireless technologies which allow transmission of the derived signals by the object 100 processor 108 to a remote location(s) (i.e., processor 103 of computer system 104), where these transmitted signals can be processed, and analyzed by the program; and subsequently retransmitted back to the site of origin (i.e., object 100) for point of care intervention.

These attributes will be illustrated in this exemplary embodiment, which entails application of the present invention in the most unstable of environments—namely, the front lines of battle. Whether one wants to apply this to traditional warfare, acts of terrorism, rural environments, or everyday emergency response; the same principles and applications of the present invention remains the same.

In this exemplary embodiment, a soldier has been critically wounded in combat and is found by the medic unconscious and hypotensive. Preliminary assessment reveals ballistic injury to the abdomen, blunt chest trauma, and unstable vital signs associated with massive blood loss. The medic is tasked with the difficult decision of determining survivability and if that is possible, what emergent steps are required for stabilization prior to transport to a field hospital for definitive treatment.

In order to determine the full extent of injuries in the field, whole body imaging is required, which would not be available with conventional portable medical imaging technology. Applying the apparatus and methods of the present invention, the medic removes an ampule containing thousands of specialized microbots/nanobots 100 and injects the contents intravenously after establishing access via the patient's femoral vein.

While these circulating object 100 signal emitters 101 and/or receivers 106/107 can generate whole body images on their own, the circulating objects 100 can also be supplemented by placing a specialized garment 200 over the soldier (which can be whole-body or partial in nature). In addition to embedded signal receivers 203 in this garment, the garment also contains embedded transmitters 220, whose function is to transmit the signals received to a remote location (i.e., computer system 104) for further processing and analysis by the program of processor 103. The size limitations intrinsic to the internal circulating microbots 100 and nanobots 100 do not exist with such an external garment 200, providing object 100 signal receivers 220 and/or transmitters 203 of far greater size.

In one embodiment, while not essential to function, the garment 200 may also contain miniaturized storage devices 222 which serve as a local storage device for the signals received via the signal receivers 220. This would be analogous to a Holter monitor, which records cardiac electrical activity over a prolonged time period and stores this data locally for future analysis.

In one embodiment, as continuous signals are emitted and received by the object 100, the object 100 transmitters 101 function to transmit this real-time and continuous data stream to the computer processor 103 for the program's further processing and analysis. Depending upon the architecture of the computer system 103 and distance requirements, one or multiple remote data processing locations (i.e., relay stations) may be required before the data reaches its ultimate destination, where comprehensive data analysis and graphical representation can be performed by the program. This would be analogous to multiple nodes on an extended computerized network.

In one embodiment, a variety of wireless communication transmissions and technologies may be applied for transmission of this signal data including (but not limited to) Bluetooth, satellite, infrared, light wave, radiofrequency, microwave, and ZigBee. As new technologies are developed and refined, these will continue to increase the number and availability of communication options which can be applied to the invention.

In one embodiment, as the local patient signal data is transmitted by the object 100 via external receiver 102, for example, using one of these wireless technologies, it is forwarded to one or more relay stations (not shown) and ultimately to its final destination, which could potentially be hundreds or even thousands of miles away. Once these wireless transmissions reach their ultimate destination, the signals are stored in a database 118, processed by processor 103, and analyzed by the program, remotely. Since the data being created locally is continuous in nature, the resulting imaging data (i.e., 4-D visualization maps) is being continuously updated by the program.

In one embodiment, since the present invention has the potential for bidirectional (i.e., send and receive) capabilities, the data processed by the program is subsequently transmitted back to the site of origin (i.e., object 100), using the same secure wireless communication network and technologies. The same transmitters contained within the patient garment 200 also have receive capabilities and function as wearable send transmitters 203 and receivers 220. In addition, the medic may have a separate portable video receive and display device which he/she can use to display and navigate the continuously updated 4-D visualization maps created by the program.

In one embodiment, an interesting and unique application of the present invention is the ability to project or superimpose imagery (i.e., 1D, 2D, 3D or 4D) from the program-created visualization maps directly onto the patient (i.e., superficial mapping). Using augmented reality goggles, the medic can use the projected visualization mages which have been superimposed onto the patient for performing real-time intervention through augmented image guidance and navigation.

In one embodiment, by creating the ability to store, process, analyze, and display the signal data remotely using the program, the present invention also provides the ability for remote diagnosis and intervention. In this exemplary embodiment, the real-time and continuously updated 4-D visualization maps created by the program and obtained on the battlefield, can be analyzed by remotely located experts (e.g., trauma surgeons, interventional radiologists), who in turn can directly communicate with the medic for medical decision making, as it relates to diagnosis, intervention, and treatment planning.

In one embodiment, these remote experts also have the capability of direct remote intervention, which can take place through the introduction of smart medical devices 100 into the patient. This would be analogous to remote piloting of military drones, in which the navigation and operation of the drones are remotely performed through secure wireless networks. An example of this remote intervention will be subsequently described.

Returning to the exemplary embodiment of the wounded soldier in the battlefield, the program-processed 4-D visualization maps are reviewed by both the on-site medic and remote medical experts, who have the ability to directly communicate with one another. (In addition, the data can also be processed by the program through use of AI (e.g., computer-aided diagnosis software) to assist in diagnosis. In the exemplary embodiment, the program's analysis reveals the following diagnoses:

1. Multiple displaced right rib fractures.
2. 40% right pneumothorax (i.e., lung collapse).
3. Liver laceration with active bleeding
4. Hemoperitoneum (i.e., blood in peritoneal cavity).

In this exemplary embodiment, since the patient is hemodynamically unstable and in shock, the medic establishes intravenous and intra-arterial access and begins administering fluids along with pain medication. With the assistance of remote radiology and trauma surgical experts, the diagnoses are discussed among the surgical experts and an interventional strategy is discussed. The two most important requirements are to: 1) decompress the pneumothorax, and 2) minimize intra-abdominal bleeding in association with the liver laceration.

In conventional practice, treatment of pneumothorax is performed by inserting a needle or catheter into the pleural space (often under image guidance), to evacuate the pneumothorax and re-expand the lung. The challenge in the field is that this procedure is highly operator dependent and without conventional image guidance assistance, has a high complication rate.

In this exemplary embodiment, rather than blindly inserting needles, the medic is instructed to use the superficial mapping application of the present invention. Once the program is activated, the program-created 3-D visualization map is projected onto the patient and is synchronized with the augmented reality goggles. The area of pathologic concern (i.e., right lung) is designated as the anatomic area of primary concern, resulting in enhanced 3-D visualization detail over the right lung by the program. This provides the medic with visual guidance for placement of the needle, along with 4-D near real-time updates, demonstrating change over time.

In the exemplary embodiment, the remote surgical team provides audio assistance as the medic prepares to insert the needle, using the program-created, projected visualization map, as guidance. Once the needle has reached the target site, the abnormal air collection is aspirated, and a catheter placed through the needle for continued drainage. While the procedure is being performed, continuous dynamic real-time data is being collected and processed by the program, resulting in continuously updated 4-D visualization maps created by the program. Once the procedure has been successfully completed, the focus of attention turns to the liver laceration and its associated bleeding.

In this exemplary embodiment, this injury is far more serious and difficult to treat in the field since it is customarily treated with surgery, which is currently not possible. If the bleeding can be controlled, the patient would be a candidate for evacuation to a field hospital, but if it cannot, the patient will likely die.

In this exemplary embodiment, the 4-D visualization data created by the program, provides a number of salient diagnostic information including liver and arterial anatomy, the location and specific features of liver injury, the specific location/s of arterial bleeding, the rate of bleeding, and the volume of blood within the peritoneal cavity (as well as its expansion rate). This information serves to facilitate accurate diagnosis, identify intervention options and strategies, and quantify the response to treatment in real-time.

In this exemplary embodiment, based upon the severity and location of injury, the number of viable options is limited. After review and quantification of the imaging data and associated pathology, it is determined by the program (or the user) that the best intervention option is to attempt to occlude the right hepatic artery, which is serving as the source of bleeding. In order to attempt this in the field, a smart medical device 410 is to be inserted via the arterial access line and actively navigate this device 410 to the origin of the right hepatic artery.

In this exemplary embodiment, even with the assistance of augmented reality, the planned intervention is beyond the training and expertise of the medic so it is mutually decided to have the intervention performed remotely by the trauma surgeons and radiologists, working in tandem. As the 4-D visualization maps and associated quantitative measurements are continuously updated by the program, the remote operators navigate the smart device 410 to the origin of the right hepatic artery.

In this exemplary embodiment, once the smart device 410 position has been verified, an anchoring device 420 is deployed, in order to stabilize positioning of the device 410. Small incremental positional changes in smart device 410 location can be actively monitored by the program with the continuous dynamic 4-D images obtained.

In this exemplary embodiment, once smart device 410 stabilization has been ensured, two miniaturized devices within the larger smart device 410 are activated. These include a miniaturized device (not shown) which deploys embolization coils and a miniaturized device 429 which injects gel foam 428, which serves as a chemical occlusion substance. Collectively, these are intended to occlude right hepatic arterial flow proximal to the active bleeding site.

In this exemplary embodiment, under continuous anatomic guidance and dynamic updates by the program, the procedure is performed with deployment of both the coils and gel foam 428. Temporal images obtained before, during, and after completion of the intervention, by the program, demonstrate on the visual display 105, a marked reduction in bleeding. This dynamic imaging by the program will continue, providing continuous feedback to the team.

In this exemplary embodiment, once the extent of active bleeding has been reduced and vital signs stabilized, it is determined by the program (or the user) that the patient is now a candidate for evacuation. During this time, continuous visualization maps are acquired and analyzed by the program to determine if additional in-flight intervention is required. The smart device 410 is kept in situ in the event that additional intervention is required. Once the patient arrives at the hospital, it can be removed and more definitive treatment performed.

By taking advantage of the rapid evolutionary changes toward technology miniaturization and enhanced computer processing, the present invention is indicated as a transformative technology which can replace existing medical imaging technologies and their inherent limitations. The creation of 4-dimensional visualization maps which provide continuous and dynamic data on both macroscopic and microscopic levels could truly become a dramatic improvement to the status quo. At the heart of the present invention are microbots and nanobots 100 and smart devices 100 which will continue to expand in functionality and performance. The adaptation of these miniaturized bots, biosensors, and computer processors to the constructs of the present invention will provide the mechanism to make the present invention transformative.

An added benefit of the present invention is the synergy it provides with smart devices 100, which are also an important and evolving medical technology. When combining these two novel technologies, one is presented with the opportunity to non-invasively transform medical diagnosis and treatment with the ability to internally navigate smart devices 100 to targeted anatomic locations.

The end result of the advantages of the present invention will be the transformation of medical imaging from a static, fixed, and macroscopic product into one which is dynamic, real-time, and microscopic in nature.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A system to create anatomic visualization maps of a body of a patient, comprising:
   a medical device, including:
   at least one of a signal emitter which emits energy in a form of a transmitted signal, or a signal receiver which receives transmitted energy as a received signal, the signal receiver including at least one sensor or an antenna;
   a plurality of sensors and/or detectors which provide real-time anatomic and physiologic data to the signal emitter;
   a passive or active propulsion mechanism; and
   an energy source; and
   an external signal receiver and/or transmitter which receives the transmitted signal;
   a controller which receives the transmitted signal from the external signal receiver and/or transmitter and converts the transmitted signal into a standardized form of data; and
   an external processor which receives the data and records the data in a database;
   wherein the external processor performs computational analysis on the data to produce a 4-D anatomic visualization map of the body showing real-time anatomic and physiologic change that is displayed on a display; and
   wherein imagery from the 4-D anatomic visualization map is projected or superimposed directly onto the patient in real-time medical intervention.

2. The system of claim 1, wherein the signal emitter emits energy in a form including at least one of chemical, electrical, radiant, sound, light, magnetic/magneto-inductive, mechanical, thermal, nuclear, motion, or elastic; and
   wherein transfer of the data is conducted by methods including at least one of near field communication (NFC), Bluetooth, infrared, microwave, Zigbee, satellite, light, or radio frequency (RF) transmission.

3. The system of claim 2, wherein the external signal receiver and/or transmitter is embedded in an article of clothing or linens proximate to the body of the patient and the medical device and is accessed by the medical device via at least one of the data transfer methods.

4. The system of claim 1, wherein the medical device is at least one of embedded in a patient or circulated within the patient in a localized anatomic region or systemically, throughout a body of the patient; and
   wherein the medical device is introduced into the body from one of a urinary bladder, lungs, bloodstream, skin, lymphatic system, or gastrointestinal tract.

5. The system of claim 1, wherein the medical device is one of a microbot, nanobot, miniaturized smart medical device, or other standard medical device including at least one of prosthesis, surgical hardware, or implant; and wherein on condition that the medical device is disposed in the body, the medical device is one of internally located and fixed or temporarily placed and/or trans- portable.

6. The system of claim 5, wherein the standard medical device is one of temporary or permanent in the body, the temporary medical device including at least one of vascular or bladder catheters, intravascular balloon pumps, drainage tubes, or short-term surgical hardware; and wherein the permanent medical device is at least one of vascular stents, pacemakers, infusion pumps, arthro- plasties, prosthetic valves, or permanent surgical hard- ware.

7. The system of claim 5, wherein the microbots and nanobots are at least one of physically or coalesced with specific cell types in the body, or tagged to targets in the body including at least one of antibodies, circulating cells including at least one of macrophages, red blood cells, platelets, or lymphocytes, genetic material, bacteria, or tumor cells.

8. The system of claim 1, wherein a plurality of medical devices is internally mapped by being positioned in prox- imity to one another internally in the body of the patient in a predetermined configuration.

9. The system of claim 1, wherein the medical device includes only signal emitters or signal receivers, or both signal emitters and signal receivers.

10. The system of claim 1, wherein the signal receiver of the medical device receives signals transmitted from at least one of the signal transmitters of other medical devices or from the external signal receiver and/or transmitter.

11. The system of claim 1, wherein transmitted signals received from the signal receivers are converted by the controller and/or the external processor into the 4D anatomic visualization map by at least one of spectroscopy, thermog- raphy, radiography and computer tomography, scintillators, magnetic resonance imaging (MRI), or ultrasound, and by at least one of iterative reconstruction, filtered back projection, convolutional neural networks, or Fourier transformation; and wherein noise and measurement errors in the data are removed by filtering techniques by the external pro- cessor including at least Kalman filters.

12. The system of claim 11, wherein the 4D anatomic visualization map is automatically created based on auto- mated signal activations initiated by the external processor, at predetermined intervals or under predetermined condi- tions including movement of the medical device from a predetermined location; and wherein the data is plotted over time by the external processor to create a dynamic 4D visualization map.

13. The system of claim 1, wherein the plurality of sensors and/or detectors includes at least one of biosensors, flow sensors, energy receptors, or distance sensors;

wherein the distance sensors include at least one of ultrasonic, infrared, laser distance or time of flight light emitting diode (LED) sensors;

wherein the distance sensors derive distance by measuring at least one of a time between signal transmission and receipt by the signal receiver of at least one of an intensity of the signal transmission or a pulse change; and wherein the medical device navigates in the body based on a continuous feedback of transmitted signals to the signal receiver from other medical devices or the external transmitter/receiver, or from transmitted sig- nals from within a target location.

14. The system of claim 1, wherein the active propulsion mechanism includes a propulsion device activated by a propulsion activation mechanism to position the medical device, the propulsion device including at least one of chemically powered motors, enzymatically powered motors, external field driven motors, internally mounted miniatur- ized electrodes, miniaturized electromagnetic pumps, or appendages, activated by a propulsion activation mecha- nism.

15. The system of claim 1, wherein the transmitted signal is unique to each medical device and signal differentiation between a plurality of medical devices is accomplished by analysis of alteration in signal type, strength, direction, transmission time, frequency, or pattern.

16. The system of claim 1, wherein the 4D anatomic visualization map is created with other data sources in combination to produce a hybrid visual display, the other data sources including at least one of MRI spectroscopy, positron emission and computed tomography (PET-CT), or multispectral optoacoustic tomography.

17. The system of claim 1, wherein the medical device further comprises:

a reservoir and/or a tool disposed in a recess; and a deployment mechanism to deploy the tool from the recess;

wherein the tool performs a plurality of actions including at least one of localized drug delivery, biopsy, micro- surgery, thermal ablation, cryotherapy, embolization, or cauterization.

18. The system of claim 1, wherein expanded temporal analysis is performed by the controller to render at least one 4-D anatomic visualization map which shows maximum change by temporal subtraction which visualizes changes in anatomy and pathology over a predetermined period of signal analysis.

19. A system to create anatomic visualization maps of a body of a patient comprising:

a medical device, including:

at least one of a signal emitter which emits energy in a form of a transmitted signal, or a signal receiver which receives transmitted energy as a received signal, the signal receiver including at least one sensor or an antenna;

a plurality of sensors and/or detectors;

a passive or active propulsion mechanism; and an energy source; and an external signal receiver and/or transmitter which receives the transmitted signal;

a controller which receives the transmitted signal from the external signal receiver and/or transmitter and converts the transmitted signal into a standardized form of data; and an external processor which receives the data and records the data in a database;

wherein the external processor performs computational analysis on the data to produce a 4-dimensional (4D) anatomic visualization map of the body that is dis- played on a display;

wherein a plurality of medical devices is internally mapped by being positioned in proximity to one another internally in the body of the patient in a predetermined configuration;

wherein the medical device includes an internal processor and at least one of the internal processor and/or the external processor determines a relative positioning of each medical device in relation to each other by analyzing metrics including at least one of distance, speed, or direction of travel of the transmitted signal, and thereby continuously updating the location of each medical device; and wherein the computational analysis of the external processor includes a location of the medical device in 3-dimensional (3D) space which is achieved by one of triangulation or predetermined frequency of the transmitted signal.

20. A system to create anatomic visualization maps of a body of a patient, comprising:

a medical device, including:

at least one of a signal emitter which emits energy in a form of a transmitted signal, or a signal receiver which receives transmitted energy as a received signal, the signal receiver including at least one sensor or an antenna;

a plurality of sensors and/or detectors;

a passive or active propulsion mechanism; and an energy source; and an external signal receiver and/or transmitter which receives the transmitted signal;

a controller which receives the transmitted signal from the external signal receiver and/or transmitter and converts the transmitted signal into a standardized form of data; and an external processor which receives the data and records the data in a database;

wherein the external processor performs computational analysis on the data to produce a 4-dimensional (4D) anatomic visualization map of the body that is displayed on a display;

wherein the signal receiver of the medical device receives signals transmitted from at least one of the signal transmitters of other medical devices or from the external signal receiver and/or transmitter; and wherein one of a plurality of the medical devices or the external signal receiver and/or transmitter form a network, the plurality of medical devices forming a mesh network wherein each signal emitter of each medical device communicates only with other signal receivers of other medical devices and only one or more of the plurality of medical devices in the mesh network communicate with the controller.

21. The system of claim 20, wherein the plurality of external signal receivers and/or transmitters form a relay of external signal receivers and/or transmitters.

22. A system to create anatomic visualizations maps of a body of a patient, comprising:

a medical device, including:

at least one of a signal emitter which emits energy in a form of a transmitted signal, or a signal receiver which receives transmitted energy as a received signal, the signal receiver including at least one sensor or an antenna;

a plurality of sensors and/or detectors;

a passive or active propulsion mechanism; and an energy source; and an external signal receiver and/or transmitter which receives the transmitted signal;

a controller which receives the transmitted signal from the external signal receiver and/or transmitter and converts the transmitted signal into a standardized form of data; and an external processor which receives the data and records the data in a database;

wherein the external processor performs computational analysis on the data to produce a 4-dimensional (4D) anatomic visualization map of the body that is displayed on a display;

wherein the medical device includes an internal processor and at least one of the internal processor and/or the external processor determines a relative positioning of each medical device in relation to each other by analyzing metrics including at least one of distance, speed, or direction of travel of the transmitted signal, and thereby continuously updating the location of each medical device;

wherein at least one of the internal processor or the external processor monitors a level of energy of the energy source, and on condition that the energy source falls to a predetermined threshold, the external processor initiates recharging of the energy source via energy receptors, from external charging sources located at least one of internal or external to the body;

wherein the energy source is at least one of a battery, biofuel cell, thermoelectricity, piezoelectric generator, photovoltaic cell, or ultrasonic transducer; and wherein the external charging sources include at least one of light sources, electromagnetic fields, radiofrequency devices, ultrasound, thermal energy, sound, or vibration.

23. The system of claim 22, wherein on condition that charging of the energy source is indicated by the external processor, the medical device automatically seeks the energy source or receives instructions from the at least one of internal processor or the external processor to move to the energy source, and wherein an automated alert is sent to a user that charging of the energy source is indicated.

24. The system of claim 23, wherein the medical device is manually activated by user instruction, or automatically activated under predetermined conditions including at least one of damage to medical device structural integrity, achieving a predetermined threshold in energy source requiring charging, or manifestation of predetermined clinical conditions in the body of the patient; and wherein an automated alert is sent to the user when the predetermined conditions are met.

25. A medical device to create anatomic visualizations maps of a body of a patient, comprising:

a medical device, including:

at least one of a signal emitter which emits energy in a form of a transmitted signal, or a signal receiver which receives transmitted energy as a received signal, the signal receiver including at least one sensor or an antenna;

a plurality of sensors and/or detectors;

a passive or active propulsion mechanism; and an energy source; and an external signal receiver and/or transmitter which receives the transmitted signal;

a controller which receives the transmitted signal from the external signal receiver and/or transmitter and converts the transmitted signal into a standardized form of data; and an external processor which receives the data and records the data in a database;

wherein the external processor performs computational analysis on the data to produce a 4-dimensional (4D) anatomic visualization map of the body that is displayed on a display;

wherein transmitted signals received from the signal receivers are converted by the controller and/or the external processor into the 4D anatomic visualization map by at least one of spectroscopy, thermography, radiography and computer tomography, scintillators, magnetic resonance imaging (MRI), or ultrasound, and by at least one of iterative reconstruction, filtered back projection, convolutional neural networks, or Fourier transformation; wherein the transmitted signals are evaluated by the external processor for accuracy and reliability, and on condition that a transmitted signal is identified as not meeting predetermined standards of performance, or failure of the medical device to operate as required by the user, the medical device is instructed by the external processor to be at least one of moved to a predetermined location in the body for collection, turned off, destroyed, collected by another medical device, removed from the body as waste, or have the transmitted signal that fails to meet predetermined standards of performance ignored or bypassed by the external processor; and wherein an automated alert is sent to the user that the medical device fails to meet the predetermined standards of performance.

* * * * *